(12) United States Patent
Holaday et al.

(10) Patent No.: US 6,805,865 B1
(45) Date of Patent: Oct. 19, 2004

(54) COMPOSITIONS AND METHODS FOR TREATING CANCER AND HYPERPROLIFERATIVE DISORDERS

(75) Inventors: John W. Holaday, Bethesda, MD (US); Antonio Ruiz, Gaithersburg, MD (US); John Madsen, Jefferson, MD (US); Stacy M. Plum, Arlington, VA (US)

(73) Assignee: EntreMed, Inc., Rockville, MD (US)

( * ) Notice: Subject to any disclaimer, the term of this patent is extended or adjusted under 35 U.S.C. 154(b) by 0 days.

(21) Appl. No.: 09/266,543

(22) Filed: Mar. 11, 1999

Related U.S. Application Data

(63) Continuation-in-part of application No. 09/265,213, filed on Mar. 10, 1999, now abandoned, and a continuation-in-part of application No. 08/467,101, filed on Jun. 6, 1995, now Pat. No. 5,919,459, which is a continuation of application No. 08/271,557, filed on Jul. 7, 1994, now abandoned, which is a continuation of application No. 08/068,717, filed on May 27, 1993, now abandoned.

(60) Provisional application No. 60/077,460, filed on Mar. 10, 1998.

(51) Int. Cl.$^7$ ...................... A61K 39/395; A61K 39/00; A61K 39/385

(52) U.S. Cl. ................. 424/185.1; 424/154.1; 424/194.1; 424/195.11; 424/198.1

(58) Field of Search ................ 424/154.1, 194.1, 424/185.1, 195.11, 198.1

(56) References Cited

U.S. PATENT DOCUMENTS

| | | | |
|---|---|---|---|
| 5,252,718 A | * | 10/1993 | Baird et al. |
| 5,288,704 A | * | 2/1994 | Ungheri et al. |
| 5,629,327 A | | 5/1997 | D'Amato |
| 5,733,876 A | | 3/1998 | O'Reilly et al. |
| 5,792,845 A | | 8/1998 | O'Reilly et al. |
| 5,854,205 A | | 12/1998 | O'Reilly et al. |
| 5,919,459 A | * | 7/1999 | Nacy et al. |

FOREIGN PATENT DOCUMENTS

| | | | |
|---|---|---|---|
| EP | 0 281 822 | * | 9/1988 |

OTHER PUBLICATIONS

Kardami, E. et al. Characterization of two preparation of antibodies to basic fibroblast growth factor which exhibit distinct patterns of immunolocalization. Growth Factors, 4: 69–80, 1990.*

Baird, et al., "Receptor–and Heparin Binding Domains of Basic Fibroblast Growth Factor", *Proc. Natl. Acad. Sci. USA*, vol. 85, Apr., pp. 2324–2328 (1988).

Seaver, "Monoclonal Anigbodies in Industry: More Difficult than Originally Thought", *Genetic Engineering News*, vol. 14, Aug., pp. 10 and 21 (1994).

Soker, et al., "Neuropilin–1 is Expressed by Endothelial and Tumor Cells as an Isoform–Specific Receptor for Vascular Endothelial Growth Factor", *Cell*, vol. 92, Mar., pp. 735–745 (1998).

* cited by examiner

*Primary Examiner*—Larry R. Helms
*Assistant Examiner*—Christopher Yaen
(74) *Attorney, Agent, or Firm*—Kilpatrick Stockton LLP

(57) ABSTRACT

Compositions and methods effective for eliciting an immune response for inhibiting abnormal or undesirable cell proliferation, particularly endothelial cell proliferation and angiogenesis related to neovascularization and tumor growth are provided. The compositions comprise a naturally occurring or synthetic protein, peptide, or protein fragment containing all or an active portion of a growth factor in a pharmaceutically acceptable carrier. The preferred growth factors comprise basic fibroblast growth factor and vascular endothelial growth factor. The methods involve administering to a human or animal the compositions described herein in a dosage sufficient to elicit an- immune response. The methods are useful for treating diseases and processes mediated by undesired and uncontrolled cell proliferation, such as cancer, particularly where uncontrolled cell proliferation is influenced by the presence of growth factors. Administration of the composition to a human or animal having metastasized tumors is useful for preventing the growth or expansion of such tumors.

9 Claims, 18 Drawing Sheets

HEPARIN BINDING DOMAIN    LLA CONTROL

SEQUENCE LISTING

```
<160> NUMBER OF SEQ ID NOS: 9

<210> SEQ ID NO 1
<211> LENGTH: 45
<212> TYPE: PRT
<213> ORGANISM: Homo sapiens

<400> SEQUENCE: 1

Tyr Cys Lys Asn Gly Gly Phe Phe Leu Arg Ile His Pro Asp Gly Arg
 1               5                  10                  15
```

```
Val Asp Gly Val Arg Glu Lys Ser Asp Pro His Ile Lys Leu Gln Leu
            20                  25                  30

Gln Ala Glu Glu Arg Gly Val Val Ser Ile Lys Gly Val
            35                  40                  45

<210> SEQ ID NO 2
<211> LENGTH: 21
<212> TYPE: PRT
<213> ORGANISM: Homo sapiens

<400> SEQUENCE: 2

Ser Asn Asn Tyr Asn Thr Tyr Arg Ser Arg Lys Tyr Ser Ser Trp Tyr
 1               5                  10                  15

Val Ala Leu Lys Arg
            20

<210> SEQ ID NO 3
<211> LENGTH: 13
<212> TYPE: PRT
<213> ORGANISM: Homo sapiens

<400> SEQUENCE: 3

Cys Arg Thr Lys Pro Glu Lys Cys Asp Lys Pro Arg Arg
 1               5                  10

<210> SEQ ID NO 4
<211> LENGTH: 20
<212> TYPE: PRT
<213> ORGANISM: Homo sapiens

<400> SEQUENCE: 4

Cys Glu Cys Arg Pro Lys Lys Asp Arg Thr Lys Pro Glu Lys Cys Asp
 1               5                  10                  15

Lys Pro Arg Arg
            20

<210> SEQ ID NO 5
<211> LENGTH: 21
<212> TYPE: PRT
<213> ORGANISM: Homo sapiens

<400> SEQUENCE: 5

Ala Pro Thr Thr Glu Gly Glu Gln Lys Ser His Glu Val Ile Lys Phe
 1               5                  10                  15

Met Asp Val Tyr Cys
            20

<210> SEQ ID NO 6
<211> LENGTH: 41
<212> TYPE: PRT
<213> ORGANISM: Homo sapiens

<400> SEQUENCE: 6

Cys Glu Arg Arg Lys His Leu Phe Val Gln Thr Cys Lys Cys Ser Cys
 1               5                  10                  15

Lys Asn Thr Asp Ser Arg Cys Lys Ala Arg Gln Leu Glu Asn Glu Arg
            20                  25                  30

Thr Cys Arg Cys Asp Lys Pro Arg Arg
            35                  40

<210> SEQ ID NO 7
<211> LENGTH: 26
```

```
<212> TYPE: PRT
<213> ORGANISM: Homo sapiens

<400> SEQUENCE: 7

Cys Asn Asp Glu Gly Leu Glu Ser Val Pro Thr Glu Glu Ser Asn Ile
  1               5                  10                  15

Thr Met Gln Ile Met Arg Ile Lys Pro His
             20                  25

<210> SEQ ID NO 8
<211> LENGTH: 13
<212> TYPE: PRT
<213> ORGANISM: Homo sapiens

<400> SEQUENCE: 8

Cys Asn Asp Glu Gly Leu Glu Ser Val Pro Thr Glu Glu
  1               5                  10

<210> SEQ ID NO 9
<211> LENGTH: 16
<212> TYPE: PRT
<213> ORGANISM: Homo sapiens

<400> SEQUENCE: 9

Cys Glu Glu Ser Asn Ile Thr Met Gln Ile Met Arg Ile Lys Pro His
  1               5                  10                  15
```

COMPOSITIONS AND METHODS FOR TREATING CANCER AND HYPERPROLIFERATIVE DISORDERS

CROSS-REFERENCE TO RELATED APPLICATIONS

The present application is a continuation-in-part application of U.S. patent application Ser. No. 09/265,213 filed Mar. 10, 1999 (now abandoned) which is a non-provisional application of U.S. Provisional Patent Application Ser. No. 6/077,460 filed Mar. 10, 1998. The present application is also a continuation-in-part application of 08/467,101, filed Jun. 6, 1995, now U.S. Pat. No 5,919,459 issued on Jul. 6, 1999, which is a continuation application of U.S. patent application Ser. No. 08/271,557 filed Jul. 7, 1994 (now abandoned), which is a continuation of U.S. patent application Ser. No. 08/068,717 filed May 27, 1993 (now abandoned).

TECHNICAL FIELD

The present invention relates to methods and compositions for preventing or reducing cancers in humans or animals. More particularly, the present invention relates to immunogenic compositions comprising growth factors, active fragments thereof, antibodies specific for growth factors, and methods of use thereof.

BACKGROUND OF THE INVENTION

While many cancers are treatable by chemotherapeutic agents, a significant number of cancers are intrinsically drug resistant and others acquire resistance during or following chemotherapy. Cancers frequently are resistant to more than one type of drug. This phenomenon is called multidrug resistance or MDR. Consequently, there is a great need for compositions and methods that can be used in addition to, or as alternatives to, chemotherapy for the treatment of cancer.

A major clinical problem of cancer is metastasis. By the time that the primary tumor is identified and localized, seed cells often have escaped and migrated or metastasized to other organs in the body where they establish secondary tumors. Surgical procedures are rarely sufficient to cure a cancer because even after the primary tumor is removed multiple secondary tumors survive and proliferate. Consequently, there exists an immediate and pressing need for techniques of eradicating secondary tumors that already exist.

Cancer cells that escape the primary tumor are usually carried in the venous and lymphatic circulation until they lodge in a downstream capillary bed or lymph node. However, only 1 in 10,000 of the cancer cells that escape the primary tumor survive to establish a secondary tumor. Successful cancer cells are those that find a favorable environment for survival and growth. The favorable environment include hormones and growth-promoting factors. Stimulating factors include local growth factors, hormones produced by the host, and autostimulating growth factors produced by the tumor cells themselves. Consequently, there is an immediate and pressing need for techniques capable of preventing or inhibiting metastasis of cancer and the formation of secondary tumors.

Additionally, many other hyperproliferative disorders exist. Hyperproliferative disorders are caused by non-cancerous (i.e. non-neoplastic) cells that overproduce in response to a particular growth factor. Examples of such hyperproliferative disorders include diabetic retinopathy, psoriasis, endometriosis, macular degenerative disorders and benign growth disorders such as prostate enlargement and lipomas.

It is known that many new cancers are initiated, and existing cancers and hyperproliferative disorders stimulated, by growth factors that affect either the cancer cell itself, or normal tissue around the cancer that facilitate survival of the cancer cell (i.e., angiogenesis factors). There is a direct correlation between the circulating level of certain growth factors and cancer proliferation. A potential method of treatment would be to regulate the level of circulating growth factors in a patient to prevent cancer initiation or recurrence, and to reduce or eliminate existing cancers. What is needed, therefore, are compositions that remove the target growth factors from circulation or inhibit the growth-promoting activity of growth factors.

Cellular proliferation is a normal ongoing process in all living organisms and is one that involves numerous factors and signals that are delicately balanced to maintain regular cellular cycles. The general process of cell division is one that consists of two sequential processes: nuclear division (mitosis), and cytoplasmic division (cytokinesis). Because organisms are continually growing and replacing cells, cellular proliferation is a central process that is vital to the normal functioning of almost all biological processes. Whether or not mammalian cells will grow and divide is determined by a variety of feedback control mechanisms, which include the availability of space in which a cell can grow, and the secretion of specific stimulatory and inhibitory factors in the immediate environment.

When normal cellular proliferation is disturbed or somehow disrupted, the results can affect an array of biological functions. Disruption of proliferation could be due to a myriad of factors such as the absence or overabundance of various signaling chemicals, growth factors or presence of altered environments. Some disorders characterized by abnormal cellular proliferation include cancer, abnormal development of embryos, improper formation of the corpus luteum, difficulty in wound healing as well as malfunctioning of inflammatory and immune responses.

Cancer is characterized by abnormal cellular proliferation. Cancer cells exhibit a number of properties that make them dangerous to the host, often including an ability to invade other tissues and to induce capillary ingrowth, which assures that the proliferating cancer cells have an adequate supply of blood. One of the defining features of cancer cells is that they respond abnormally to control mechanisms that regulate the division of normal cells and continue to divide in a relatively uncontrolled fashion until they kill the host.

Angiogenesis and angiogenesis related diseases are closely affected by cellular proliferation and therefore cytokines and growth factors. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" is defined herein as a thin layer of flat cells that lines serous cavities, lymph vessels, and blood vessels. These cells are defined herein as "endothelial cells". The term "endothelial inhibiting activity" means the capability of a molecule to inhibit angiogenesis in general. The inhibition of endothelial cell proliferation also results in an inhibition of angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic-dependent, angiogenic-associated, or angiogenic-related diseases. These diseases are a result of abnormal or undesirable cell proliferation, particularly endothelial cell proliferation.

The hypothesis that tumor growth is angiogenesis-dependent was first proposed in 1971 by Judah Folkman (N. Engl. Jour. Med. 285:1182 1186, 1971). In its simplest terms the hypothesis proposes that expansion of tumor volume beyond a certain phase requires the induction of new capillary blood vessels. For example, pulmonary micrometastases in the early prevascular phase in mice would be undetectable except by high power microscopy on histological sections. Further indirect evidence supporting the concept that tumor growth is angiogenesis dependent is found in U.S. Pat. Nos. 5,639,725, 5,629,327, 5,792,845, 5,733,876, and 5,854,205, all of which are incorporated herein by reference.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegener's sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Thus it is clear that cellular proliferation, particularly endothelial cell proliferation, plays a major role in the metastasis of a cancer. If this abnormal or undesirable proliferation activity could be repressed, inhibited, or eliminated, then the tumor, although present, would not grow. In the disease state, prevention of abnormal or undesirable cellular proliferation and angiogenesis could avert the damage caused by the invasion of the new microvascular system. Therapies directed at control of the cellular proliferative processes could lead to the abrogation or mitigation of these diseases.

What are needed are compositions and methods which can inhibit abnormal or undesirable cellular proliferation related to tumors. The compositions should be able to overcome the activity of endogenous growth factors in premetastatic tumors and prevent the dissemination of cancerous cells thereby inhibiting the development of disease and the growth of tumors. The compositions should also be able to modulate the formation of capillaries in angiogenic processes, such as wound healing and reproduction. Finally, the compositions and methods for inhibiting cellular proliferation should preferably be non-toxic and produce few side effects.

SUMMARY OF THE INVENTION

The present invention generally comprises methods and compositions for preventing or treating cancers. More particularly, the present invention involves immunogenic growth factor-containing compositions comprising growth factors or active fragments thereof and delivery vehicles. Though not wishing to be bound by the following theory, the compositions of the present invention may elicit either a cellular or immune response that results in the prevention and reduction of cancer.

The present invention provides a method of vaccinating a human or animal against growth factors that are associated with specific cancer types and hyperproliferative disorders. Certain cancers are associated with only one growth factor whereas other cancers are regulated several by growth factors. For example, certain T cell lymphomas produce the growth factor IL-2, which stimulates proliferation by autocrine action; other tumors produce factors that promote angiogenesis and stimulate growth of metastatic cancer lesions by inducing vascularization of tissue at the site of metastases.

Examples of growth factor-containing compositions comprise delivery or carrier vehicles such as liposomes or vesicles having portions of growth factor, growth factor fragments, synthetic peptides of certain epitopes of growth factors, or modified growth factor fragments presented on their external surfaces. In an alternative embodiment a growth factor, or immunogenic fragment thereof, may be partially or totally encapsulated with a carrier such as a liposome. In another alternative embodiment of the present invention, the growth factors or active portions thereof may be transported to desired sites by delivery mechanisms comprising the use of colloidal metals such as colloidal gold. The above described compositions are useful as vaccines to induce immunity against growth factors which otherwise are recognized as "self" by the immune system and are not naturally antigenic. The compositions are further useful in therapeutic regimens for reducing the proliferation of tumor cells. Though not wishing to be bound by the following theory, it is thought that the resulting circulating antibodies bind growth factor and thereby prevent the initiation of cancer proliferation, reduce existing cancer, or inhibit the spread of cancers.

The present invention also comprises isolated and recombinant antibodies specific for growth factors. Isolated antibodies are produced by, and purified from humans or animals with strong immune systems, and injected into humans or animals with weak or non-functional immune systems in need of such circulating antibodies. Thus, according to the present invention, cancers are reduced or inhibited either by active immunization of an individual using antigenic growth factor-containing compositions, or by passive immunization via administering an antibody or a group of antibodies specific for growth factor epitopes. Additionally, patients are immunized with the growth factor composition prior to the initiation or recurrence after treatment of cancer.

Accordingly, it is an object of the present invention to provide methods and compositions for reducing cancer and inhibiting tumor growth in a human or animal having cancer.

It is another object of the present invention to provide methods and compositions for treating and preventing the occurrence or spread of cancer.

It is a further object of the present invention to provide methods and compositions for reducing cancer and inhibiting tumor growth in a human or animal having cancer by eliciting an active cellular and humoral response in the host.

Another object of the present invention is to provide methods and compositions for reducing and preventing the occurrence of hyperproliferative disorders.

It is yet another object of the present invention to provide methods and compositions for vaccinating a human or animal against selected growth factors.

It is yet another object of the present invention to provide methods and compositions for passively immunizing a human or animal against selected growth factors.

Another object of the present invention is to provide growth factor-containing compositions that are antigenic and elicit an immune response against growth factor in humans or animals.

Another object of the present invention is to provide a vaccine composition comprising a growth factor that is non-immunogenic in a human or animal to be immunized with the composition; and a carrier wherein the growth factor is presented on the surface of the carrier such that the composition is immunogenic for the growth factor when administered into the human or animal.

It is yet another object of -the present invention to provide a growth factor containing composition wherein the growth factor comprises fibroblast (FGF), interleukins, kerotinocyte growth factor, colony stimulating factors, epidermal growth factor (EGF), vascular endothelial growth factor (VEGF), transforming growth factors, Schwann cell-derived growth factor, nerve growth factor (NGF), platelet-derived growth factor (PDGF), insulin-like growth factors 1 and 2 (IGF-1 and IGF-2), glial growth factor, tumor necrosis factors, prolactin and growth hormone.

Yet another object of the present invention is to provide growth factor peptide fragments modified with antigenic moieties to increase an individual's response to growth factor and methods of use thereof.

It is yet another object of the present invention to provide growth factor containing compositions wherein the carrier for the growth factor comprises a liposome.

It is another object of the present invention to provide growth factor containing compositions wherein the carrier for the growth factor comprises a colloidal metal.

Another object of the present invention is to provide growth factor containing compositions wherein the carrier is a baculovirus-derived vesicle.

It is yet another object of the present invention to provide growth factor peptide fragments and growth factor peptide fragments in liposomes.

It is still another object of the present invention to provide growth factor peptide fragment-containing compositions in combination with pharmaceutically acceptable adjuvants to stimulate the immune response.

It is yet another object of the present invention to provide compositions and methods for treating diseases and processes that are mediated by angiogenesis including, but not limited to, hemangioma, solid tumors, blood borne tumors, leukemia, metastasis, telangiectasia, psoriasis, scleroderma, pyogenic granuloma, myocardial angiogenesis, Crohn's disease, plaque neovascularization, arteriovenous malformations, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

Another object of the present invention is to provide anti-growth factor antibodies useful for passively immunizing a human or animal against growth factor.

Yet another object of the present invention is to provide growth factor containing compositions that may be administered intramuscularly, intravenously, transdermally, orally, or subcutaneously.

These and other objects, features and advantages of the present invention will become apparent after a review of the following detailed description of the disclosed embodiment and the appended claims.

Figure 17:
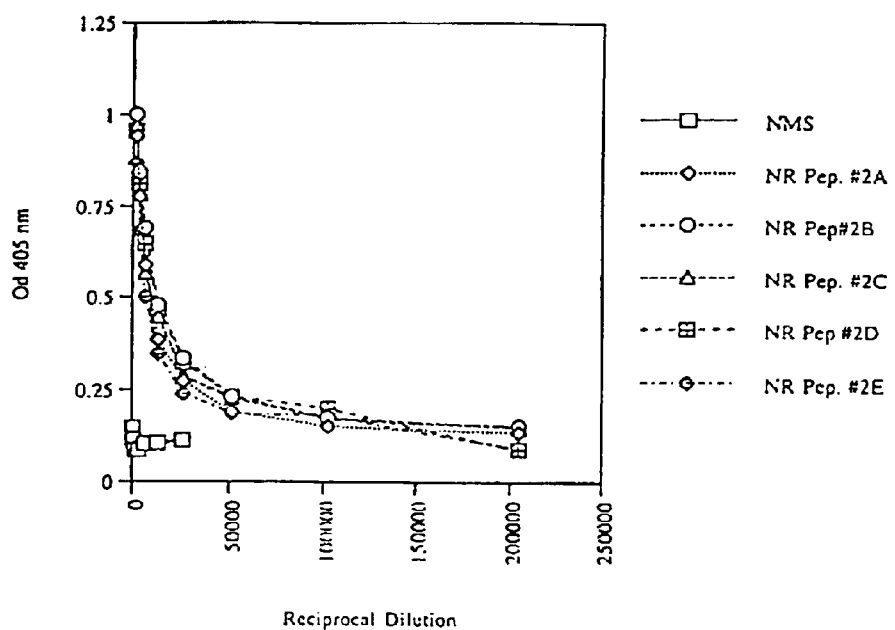
Figure 17:
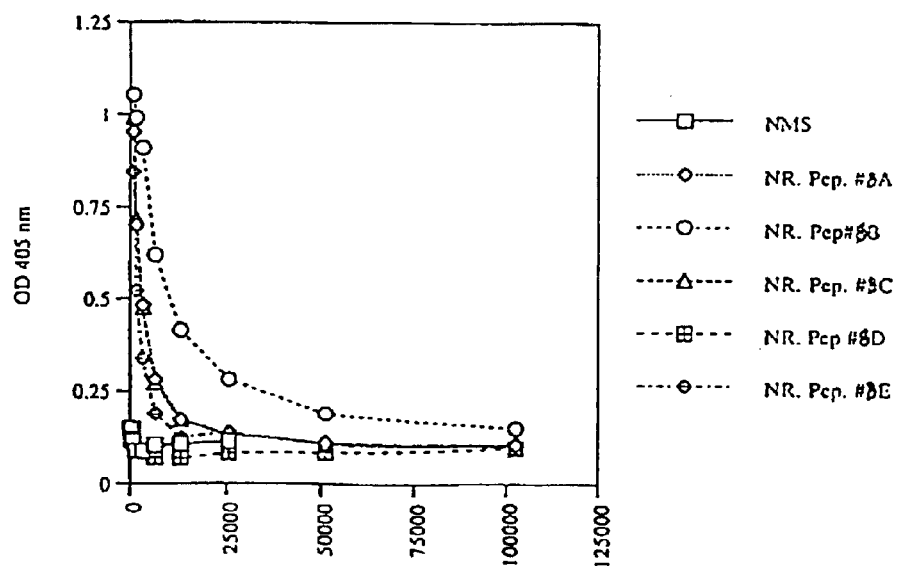

FIGS. 17(a) and 17(b) are graphs showing immunoreactivity of test peptides to autologous peptide fragments of VEGF. As discussed in Example 13, Balb/cByJ mice were vaccinated with liposomes containing VEGF peptides 2 and 3, incorporated in the liposome by simple encapsulation according to the protocols outlined in the present invention. Serum from individual mice was collected on day 35, serially diluted, and analyzed for reactivity to autologous peptide fragments of VEGF by measuring absorbance in an ELISA assay. The NMS control demonstrates the reactivity of serum from non-vaccinated mice and is not different from the reactivity of serum from mice vaccinated with a liposome control.

Figure 18:
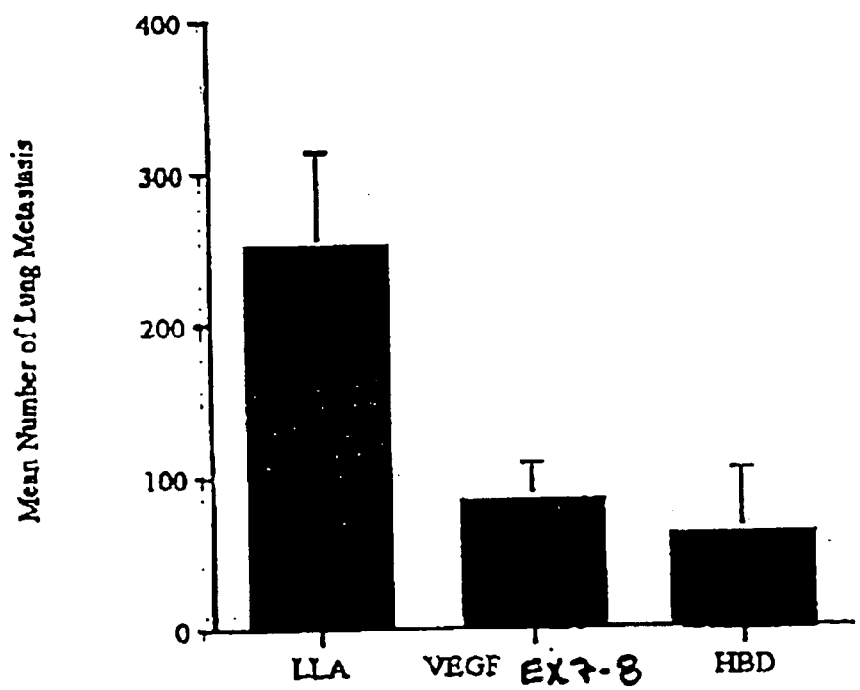

FIG. 18 provides a graph comparing the inhibitory effects on the growth and development of B16BL6 experimental metastasis in mice vaccinated with lipid liposomal A, VEGF peptide SEQ ID. NO: 6 and heparin binding domain peptide of bFGF.

DETAILED DESCRIPTION OF THE PRESENT INVENTION

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference including U.S. Provisional Application Serial No. 60/077,460, filed on Mar. 10, 1998.

The present invention comprises methods and compositions for preventing or reducing cancer and hyperproliferative disorders in a human or animal. The antigenic growth factor-containing compositions of the present invention include, but are not limited to, growth factor containing carriers, such as liposomes and vesicles, antigenic growth factors and peptide fragments thereof, antigenic growth factor peptide fragments combined with adjuvants, modified growth factor peptide fragments, modified growth factor peptide fragments combined with adjuvants, carriers containing growth factor peptide fragments, and carriers containing modified growth factor peptide fragments. Still further, the present invention comprises antibodies and other cellular responses directed against, and specific for growth factors. The present invention also includes ribonucleic acid sequences that code for the above proteins and the use of the ribonucleic acid sequences to transfect animals or humans to introduce the antigenic protein into the system and thereby causing the body to mount an immune response to the antigenic growth factor.

Definitions

The terms "a", "an" and "the" as used herein are defined to mean one or more and include the plural unless the context is inappropriate.

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" refers to an amino acid (D or L) or an amino acid mimetic incorporated in a oligopeptide by an amide bond or amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The terms "antibody" or "antibodies" as used herein include monoclonal antibodies, polyclonal, chimeric, single chain, bispecific, simianized, and humanized antibodies as well as Fab fragments, including the products of an Fab immunoglobulin expression library.

The term "antigen" refers to an entity or fragment thereof which can induce an immune response in a animal. The term includes immunogens and regions responsible for antigenicity or antigenic determinants.

As used herein, the term "soluble" means partially or completely dissolved in an aqueous solution.

As employed herein, the phrase "biological activity" refers to the functionality, reactivity, and specificity of compounds that are derived from biological systems or those compounds that are reactive to them, or other compounds that mimic the functionality, reactivity, and specificity of these compounds. Examples of suitable biologically active compounds include enzymes, antibodies, antigens and proteins.

The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions.

The phrase "consisting essentially of" is used herein to exclude any elements that would substantially alter the essential properties of the peptides to which the phrase refers. Thus, the description of a peptide "consisting essentially of . . ." excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and;
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, antiproliferative peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the proteins and peptides of the present invention are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the antiproliferative peptides described herein. Techniques for solid phase synthesis are known to those skilled in the art.

Alternatively, the antigenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the immunogenic peptide and then to cause the peptide to re-fold into the preferred conformation. Methods of reducing and denaturing proteins and inducing re-folding are well known to those of skill in the art.

As used herein, the term "growth factor" refers to growth factors, and polypeptide angiogenesis factors, and modified derivatives and peptide fragments thereof. The term "growth factor" comprises:

Fibroblast growth factor (FGF);
Interleukins 1–12 (IL-1$\alpha$, $\beta$, IL-2, IL-3, IL-4, IL-5, IL-6, IL-7, IL-8, IL-9, IL-10, IL-11, IL-12);
Kerotinocyte growth factor;
Colony stimulating factors such as, Granulocyte Colony Stimulating Factor (G-CSF), Macrophage Colony Stimulating Factor (M-CSF or CSF-1), and GM-CSF;
Epidermal Growth Factor (EGF);
Vascular Endothelial Growth Factor (VEGF, otherwise known as Vascular Permeability Factor);
Transforming Growth Factor $\alpha$ (TGF-$\alpha$);
Transforming Growth Factor $\beta_1$ through $\beta_5$ (TGF-$\beta$);
Schwann cell-derived Growth Factor;
Nerve Growth Factor (NGF);
Platelet-derived Growth Factor (PDGF);
Insulin-like Growth Factors 1 and 2 (IGF-1 and IGF-2);
Glial Growth Factor;
Tumor Necrosis Factor $\alpha$ and $\beta$ (TNF-$\alpha$, TNF-$\beta$);
Prolactin;
Prostaglandins; and
Growth hormone The molecular characterization of basic and acidic fibroblast growth factors (FGFs) has confirmed the existence of two classes of closely related angiogenic factors. Acidic and basic FGFs (hereafter aFGF and bFGF) have been identified in many molecular forms that are products of proteolytic processing at homologous sites. FGFs are associated with numerous physiological functions such as reproduction, growth, and development. The identification of specific functional domains in the primary structure of bFGF has been examined by Baird et al. (Proc. Natl. Acad. Sci. USA 85 (1988)), which is in herein incorporated by reference.

Basic fibroblast growth factor (bFGF) is an important stimulator of angiogenesis implicated in neoplastic progression. As demonstrated by Examples 1–14, two synthetic peptides, one derived from the heparin-binding domain, the other from the receptor binding domain of bFGF inhibited bFGF stimulated HUVEC proliferation in vitro. C57BL/6J mice were separately vaccinated with the synthetic peptides covalently conjugated to liposomal vesicles containing lipid A. Serum analysis revealed an antibody response in mice immunized with the heparin-binding domain peptide but no antibody response in mice vaccinated with control liposomes or receptor binding domain peptides conjugated to liposomes. To determine if vaccination affects of bFGF stimulated responses in vivo, gelatin sponges containing bFGF were implanted onto livers of vaccinated mice. Histological analysis of the sponges showed absence of cellular infiltration and neovascularization of the sponges in mice vaccinated with heparin-binding domain peptide. Accordingly, growth factor vaccines comprising immunogenic, particularly heparin-binding domain peptides of bFGF, may be used to stimulate an immune response that correlates with inhibition of a bFGF stimulated in vivo response.

Vascular endothelial growth factor (VEGF) is a major regulator of angiogenesis and is involved in processes including vasculogenesis and vascular permeability. VEGF is a 40–45K homodimer and has an amino acid sequence that, in a limited fashion, is similar to that of platelet-derived growth factor (see Soker et al. *Cell*, 92:735–745 (1998) which is incorporated herein in its entirety). As demonstrated in Example 14, previously unidentified immunogenic fragments of VEGF may be administered to elicit an active immune response in a host resulting in the inhibition of growth of a tumor and reduction of cancer.

Also as used herein, the term "immunogenic" refers to substances which elicit or enhance the production of antibodies, T-cells and other reactive immune cells directed against an endogenous growth factor and contribute to an immune response in humans or animals.

An individual may have circulating antibodies directed against endogenous growth factors yet the individual does not experience an immune response against the growth factor. Thus, the term "non-immunogenic" as used herein refers to endogenous growth factor in its native state which normally elicits no, or only minimal levels of, circulating antibodies, T-cells, or reactive immune cells, and which normally does not elicit in the individual an immune response against itself. An immune response occurs when an individual produces sufficient antibodies, T-cells and other reactive immune cells against administered growth factor compositions of the present invention to moderate or alleviate the cancer or hyperproliferative disorder to be treated.

The term "carrier" as used herein means a structure in which growth factor or a growth factor fragment can be incorporated into or can be associated with, thereby presenting or exposing growth factor or part of the growth factor to the immune system of a human or animal and rendering the growth factor-carrier composition antigenic for endogenous growth factor(s). The term "carrier" further comprises methods of delivery wherein growth factor or growth factor fragment compositions may be transported to desired sites by delivery mechanisms. One example of such a delivery system utilizes colloidal metals such as colloidal gold (see PCT/US94/03177 filed Mar. 18, 1994 which is incorporated herein in its entirety).

In addition, the term "carrier" further comprises vaccine delivery mechanisms known to those skilled in the art including, but not limited to, keyhole limpet hemocyanin (KLH), bovine serum albumin (BSA) and other adjuvants. It is also to be understood that the antigenic growth factor-containing compositions of the present invention can further comprise adjuvants, preservatives, diluents, emulsifiers, stabilizers, and other components that are known and used in vaccines of the prior art. Any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX®. (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

Carrier proteins that can be used in the antigenic growth factor-containing compositions of the present invention include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

Further, the term "effective amount" refers to the amount of growth factor which, when administered to a human or animal, elicits an immune response, prevents cancer, causes a reduction in cancer or inhibits the spread and proliferation of cancer. The effective amount is readily determined by one of skill in the art following routine procedures.

For example, immunogenic growth factor compositions may be administered parenterally or orally in a range of approximately 1.0 $\mu$g to 1.0 $\mu$g per patient, though this range is not intended to be limiting. The actual amount of growth factor composition required to elicit an immune response will vary for each individual patient depending on the immunogenicity of the growth factor composition administered and on the immune response of the individual. Consequently, the specific amount administered to an individual will be determined by routine experimentation and based upon the training and experience of one skilled in the art.

The growth factor-containing compositions of the present invention are used to produce antibodies directed against portions of growth factor rendered immunogenic by their presentation in the carrier. Anti-growth factor antibodies are administered to individuals to passively immunize them against growth factor and thereby prevent the initiation of cancer growth, reduce existing cancer or inhibit the proliferation of cancer.

In one embodiment, the present invention encompasses growth factor inserted into carriers, such as membranous carriers, so as to present on the carrier surface portions of growth factor. The growth factor normally is not immunogenic because it is recognized by the immune system as "self." However, inserting portions of growth factor into the surface of liposomes alters the presentation of the growth factor to the immune system, rendering it immunogenic.

Immunogenic growth factor-containing liposomes may be made by reconstituting liposomes in the presence of purified or partially purified growth factor. Additionally, growth factor peptide fragments may be reconstituted into liposomes. The present invention also includes growth factor and growth factor peptide fragments modified so as to increase their antigenicity. For example, antigenic moieties and adjuvants may be attached to or admixed with the growth factor. Examples of antigenic moieties and adjuvants include, but are not limited to, lipophilic muramyl dipeptide derivatives, nonionic block polymers, aluminum hydroxide or aluminum phosphate adjuvant, and mixtures thereof.

The present invention further encompasses growth factor fragments modified with hydrophobic moieties, such as palmitic acid, that facilitate insertion into the hydrophobic lipid bilayer of a carrier. Hydrophobic moieties of the present invention may be fatty acids, triglycerides and phospholipids wherein the fatty acid carbon back bones has at least 10 carbon atoms. Most preferable are lipophilic moieties having fatty acids with a carbon backbone of at least approximately 14 carbon atoms and up to approximately 24 carbon atoms. The most preferred hydrophobic moieties have a carbon backbone of at least 14 carbon atoms. Examples of hydrophobic moieties include, but are not limited to, palmitic acid, stearic acid, myristic acid, lauric acid, oleic acid, linoleic acid, and linolenic acid. The most preferred hydrophobic moiety is palmitic acid.

Immunogenic compositions containing growth factor, modified growth factor, and peptide fragments thereof are administered to a human or animal to induce immunity to growth factor. The immunized human or animal develops circulating antibodies against growth factor which bind to growth factor, thereby reducing or inactivating its ability to stimulate cancer cell proliferation.

Liposomes with growth factor inserted into the membrane, as well as other immunogenic compositions containing growth factor, also are used to produce a panel of monoclonal or polyclonal antibodies that are specific for growth factor. Antibodies are made by methods well known to those of ordinary skill in the art. Anti-growth factor antibodies bind growth factor when administered to individuals, reducing the effective circulating concentration of growth factor. Consequently, growth factor-dependent proliferation of cancer is prevented, reduced or inhibited.

The growth factor-containing compositions and anti-growth factor antibodies are administered to a human or animal by any appropriate means, preferably by injection. For example, growth factor reconstituted in liposomes is administered by subcutaneous injection. Whether internally produced or provided from external sources, the circulating anti-growth factor antibodies bind to growth factor and reduce or inactivate its ability to stimulate cancer cell proliferation.

Liposomes that can be used in the compositions of the present invention include those known to one skilled in the art. Any of the standard lipids useful for making liposomes may be used. Standard bilayer and multi-layer liposomes may be used to make compositions of the present invention. While any method of making liposomes known to one skilled in the art may be used, the most preferred liposomes are made according to the method of Alving et al., Infect. Immun. 60:2438–2444, 1992, hereby incorporated by reference. The liposome can optionally contain an adjuvant. A preferred adjuvant is detoxified lipid A, such as monophosphoryl or diphosphoryl lipid A.

When the vesicles are liposomes, the growth factor generally has a hydrophobic tail that inserts into the liposome membrane as it is formed. Additionally, growth factor can be modified to contain a hydrophobic tail so that the growth factor can be inserted into the liposome. For example, the growth factor gene is fused to a oligonucleotide sequence coding for a hydrophobic tail. The modified gene is inserted and expressed in an expression system, using methods known in the art, yielding a growth factor fusion protein having a hydrophobic tail. Alternatively, growth factor is exposed on the surface of previously formed liposomes by chemical attachment or electroinsertion.

When the vesicles are baculovirus-derived vesicles, recombinant growth factor is expressed on the membrane of the insect cell as a natural consequence of processing by the infected insect host cell. As with the liposome embodiment described above, growth factor may be modified so that the recombinantly expressed protein contains a hydrophobic portion to facilitate insertion into the vesicle membrane.

Growth Factor Antibodies

The antibodies provided herein are monoclonals or polyclonal antibodies having binding specificity for growth factors such as bFGF and VEGF, and antigenic peptides and fragments thereof. Preferred antigenic fragments comprise peptides having amino acid sequences set forth in SEQ ID NOS: 1–9. Most preferred antibodies are monoclonal antibodies, due to their higher specificity for the antigen. The antibodies are antigen specific and exhibits minimal or no crossreactivity with other growth factor proteins or peptides.

The monoclonal antibodies of the present invention are prepared by immunizing an animal, such as a mouse or rabbit, with a whole growth factor (such as bFGF) or immunogenic fragment thereof (such as the heparin binding domain peptide of bFGF). Spleen cells are harvested from the immunized animals and hybridomas generated by fusing sensitized spleen cells with a myeloma cell line, such as murine SP2/O myeloma cells (ATCC, Manassas, Va.). The cells are induced to fuse by the addition of polyethylene glycol. Hybridomas are chemically selected by plating the cells in a selection medium containing hypoxanthine, aminopterin and thymidine (HAT).

Hybridomas are subsequently screened for the ability to produce monoclonal antibodies against specific growth factors or related proteins and fragments. Growth factors and related proteins and peptides used for screening purposes are obtained from analyzed specimens. Alternatively, desired growth factors may comprise recombinant peptides made according to methods known to those skilled in the art. Hybridomas producing antibodies that bind to the growth factors or protein fragments thereof, are cloned, expanded and stored frozen for future production. The preferred hybridoma produces a monoclonal antibody having the IgG isotype, more preferably the IgG1 isotype.

The polyclonal antibodies are prepared by immunizing animals, such as mice or rabbits with growth factors or protein fragments thereof as described above. Blood sera is subsequently collected from the animals, and antibodies in the sera screened for binding reactivity against the growth factor or protein fragments, preferably the antigens that are reactive with the monoclonal antibody described above.

Peptides or Protein Fragments

Growth factors, peptides or fragments thereof, containing immunogenic regions can be produced from the proteins described above and tested for immunogenic activity using techniques and methods known to those skilled in the art. For example, full length recombinant bFGF (rbFGF) can be produced using the Baculovirus gene expression system. Full length proteins can be cleaved into individual domains or digested using various methods such as, for example, the method described by Enjyoji et al. (*Biochemistry* 34:5725–5735 (1995)). In accordance with the method of Enjyoji et al., rbFGF is treated with a digestion enzyme, human neutrophil elastase, and the digest purified using a heparin column. Human neutrophil elastase cleaves bFGF into several fragments: one containing the heparin binding domain and the other containing the receptor binding domain. To produce additional fragments, the protein is preferably treated with a digestion compound, hydroxylamine, according to the method of Balian et al. (*Biochemistry* 11:3798–3806 (1972)), and the digest purified using a heparin column.

Alternatively, fragments are prepared by digesting the entire protein, or large fragments thereof exhibiting immunogenic activity, to remove one amino acid at a time. Each progressively shorter fragment is then tested for immunogenic activity. Similarly, fragments of various lengths may be synthesized and tested for immunogenic activity. By increasing or decreasing the length of a fragment, one skilled in the art may determine the exact number, identity, and sequence of amino acids within the protein that are required for immunogenic activity using routine digestion, synthesis, and screening procedures known to those skilled in the art.

Desired peptides and peptide fragments may also be obtained from commercial sources such as Infinity Biotech Research and Resources (Upland, Pa.), or Research Genetics (Huntsville, Ala.).

The active fragment is preferably a fragment containing an immunogenic portion of a whole growth factor, or immunogenic peptides thereof. Preferably, the immunogenic proteins or fragments useful for the present invention comprise bFGF, VEGF and immunogenic fragments thereof. More preferably, the immunogenic fragment comprise peptides having SEQ ID NOS: 1–9. Most preferably, the immunogenic peptide comprises the fragment having SEQ ID NO: 1. Immunogenic fragments useful for the present invention comprise:

Peptide A: YCKNGGFFLRIHPDGRVDGVREKSD-PHIKLQLQAEERGV VSIKGV (SEQ ID NO: 1)

Peptide B: SNNYNTYRSRKYSSWYVALKR (SEQ ID NO: 2)

Peptide C CRTKPEKCDKPRR (SEQ. ID NO: 3)

Peptide D CECRPKKDRTKPEKCDKPRR (SEQ. ID NO: 4)

Peptide E APTTEGEQKSHEVIKFMDVYC (SEQ. ID NO: 5)

Peptide F CERRKHLFVQTCKCSCKNTDSRCKAR-QLENERTCRCDKP RR (SEQ. ID NO: 6)

Peptide G CNDEGLESVPTEESNITMQIMRIKPH (SEQ. ID NO: 7)

Peptide H CNDEGLESVPTEE (SEQ. ID NO: 8)

Peptide I CEESNITMQIMRIKPH (SEQ. ID NO: 9)

Formulations

The naturally occurring or synthetic protein, peptide, or protein fragment, containing all or an active portion of an immunogenic protein or peptide can be prepared in a physiologically acceptable formulation, such as in a pharmaceutically acceptable carrier, using known techniques. For example, the protein, peptide or protein fragment is combined with a pharmaceutically acceptable excipient to form a therapeutic composition.

Alternatively, the gene for the protein, peptide, or protein fragment, containing all or an active portion of the immunogenic peptide, may be delivered in a vector for continuous administration using gene therapy techniques. The vector may be administered in a vehicle having specificity for a target site, such as a tumor.

The compositions of the present invention may be administered in the form of a solid, liquid or aerosol. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The dosage of the composition will depend on the condition being treated, the particular composition used, and other clinical factors such as weight and condition of the patient, and the route of administration.

The composition may be administered in combination with other compositions and procedures for the treatment of diseases. For example, unwanted cell proliferation may be treated conventionally with surgery, radiation or chemotherapy in combination with the administration of the composition, and additional doses of the composition may be subsequently administered to the patient to stabilize and inhibit the growth of any residual unwanted cell proliferation.

Diseases and Conditions to be Treated

The methods and compositions described herein are useful for treating human and animal diseases and processes mediated by abnormal or undesirable cellular proliferation, particularly abnormal or undesirable endothelial cell proliferation, including, but not limited to, hemangioma, solid tumors, leukemia, metastasis, telangiectasia psoriasis scleroderma, pyogenic granuloma, myocardial angiogenesis, plaque neovascularization, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. The method and composition are particularly useful for treating angiogenesis-related disorders and diseases by inhibiting angiogenesis.

The methods and compositions described herein are particularly useful for treating cancer, arthritis, macular degeneration, and diabetic retinopathy. Administration of the compositions to a human or animal having prevascularized metastasized tumors is useful for preventing the growth or expansion of such tumors.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Construction Of Growth Factor-Containing Recombinant Baculovirus

The baculovirus expression vector is constructed as described in Webb, N.R. et al. (1989) Proc. Natl. Acad. Sci. USA 86, 7731–7735, hereby incorporated by reference. A recombinant baculovirus containing cDNA encoding full-length growth factor under transcriptional regulation of the polyhedron promoter is produced by co-transfecting recombinant pAc-growth factor DNA with wild type Autographa californica nuclear polyhedrosis virus (AcMNPV) DNA by calcium phosphate precipitation.

EXAMPLE 2

Expression And Purification Of Growth Factor

The occlusion-negative viruses from Example I are plaque-purified and propagated in Spodoptera frugiperda 9

(Sf-9) cells. Infected Sf-9 cells are propagated in monolayers or suspension as described in Webb, N.R. et al. (1989) Proc. NatL Acad. Sci. USA 86, 7731–7735. Briefly, Sf9 cells are cultured at 27° C. in TNMFH medium, described by Summers, M.D. and Smith, (1987) A Manual of Methods for Baculovirus Expression Vectors and Insect Cell Culture Procedures (Texas Agricultural Experiment Station, College Station, Tex.), Bull. 1555, supplemented with 10% v/v heat-inactivated fetal bovine serum. Extraction and purification of the recombinantly expressed growth factor is performed standard methods.

EXAMPLE 3

Preparation Of Growth Factor-Containing Liposomes

Purified growth factor is electroinserted (Mouneime, Y., et al., 1990, Biochem., hereby incorporated by reference) or reconstituted into liposomes by standard methods known in the art. Incorporation of growth factors or fractions thereof into liposomes can include:

(a) rehydration of lyophilized liposomes of known lipid components in the presence of an aqueous solution of growth factor (or growth factor fragments) to make single- or multi-lamellar liposomes with growth factor contained in the lumen of the liposome or trapped in the aqueous layer between lipid membranes of the multi-lamellar vesicles;

(b) electroinsertion of the growth factor or fractions thereof into reconstituted liposomes, wherein the growth factor would reside in the lumen or between lipid membranes;

(c) reconstitution of prepared liposomes of known composition with lyophilized fragments of the growth factor, each fragment containing a hydrophobic tail which inserts directly into the liposome lipid bilayer such that the peptide fragment is exposed on the external surface of the liposome;

(d) conjugation of active reagents to liposomal surfaces; and (e) any other method of reconstitution or combination of active reagents that results in the production of an immune response (humoral or cellular) directed to a growth factor, fractions thereof, or synthetic peptides that mimic the composition and activity of a growth factor.

EXAMPLE 4

Preparation Of Growth Factor-Containing Baculovirus Vesicles

Growth factor-containing vesicles are produced as follows. Insect-derived vesicles containing recombinant growth factor in their membranes are obtained using a baculovirus-infected insect cell. More particularly, *Spodoptera frugiperda* IPLB-Sf21-AE clonal isolate 9 (designated Sf9) insect cells are cultured and infected with recombinant baculovirus containing a cDNA encoding the full-length growth factor as described more fully in Webb et al., Proc. Natl. Acad. Sci., 86:7731–35 (1989), and in U.S. Pat. Nos. 4,745,051 and 4,879,236 both to Smith et al., which are hereby incorporated by reference. Approximately $0.8 \times 10^6$ Sf9 cells are seeded into a 1 liter Spinner flask containing Excell media (JRH Scientific, Woodland, Calif. 95695). The cells are incubated at 27° C., 50% $O_2$ atmosphere. When the cells achieve a density of 3.5 to 4.0 million cells/ml, baculovirus containing recombinant growth factor is added at a multiplicity of 400–600 virus/cell to the media. Vesicle production commences about 24 hours after baculovirus infection. Peak vesicle formation is achieved approximately 72 hours after initial baculovirus infection. Flask contents are collected and centrifuged at approximately 1200 rpm to remove cells and debris. The supernatant containing vesicles are collected and subjected to centrifugation on 50% Percoll containing 0.1 M of sodium bicarbonate pH 8.3 at 20,000 RPM for 30 min using fixed-angle rotor. The double band is collected below an interphase between Percoll and cell culture medium and suspension is centrifuged in swing-bucket rotor at 20,000 RPM for 30 min. Two bands may be observed at the top and the bottom of the gradient with densities of 1.05 g/ml for vesicles and 1.06 g/ml for baculovirus particles. The vesicles have growth factor presented on their external surfaces and may be used for immunization. The vesicles are washed three times with 0.1 M sodium bicarbonate pH 8.3 using centrifugation at 20,000 RPM for 20 min and resuspended in the same buffer.

EXAMPLE 5

Immunization With Growth Factor-Containing Compositions

Immunogenic growth factor-containing compositions, comprising liposomes or baculovirus-derived vesicles, are injected into a human or animal at a dosage of 1–5000 μg per kg body weight. Antibody titers against growth factor are determined by ELISA, using the recombinant protein and horse-radish peroxidase-conjugated goat anti-human or animal immunoglobulins, or other serologic techniques (sandwich ELISA), or biologic activity assays (such as neutralization of natural or synthetic cytokines or growth factor assays or competition assays) as presently exist or as developed specifically for individual growth factors. Booster injections are administered as needed to achieve levels of protective antibodies sufficient to reduce or neutralize the activity of growth factors in vivo. Neutralizing titers and appropriate antibody isotypes are determined in experimental animals challenged with appropriate cancer cells.

EXAMPLE 6

Preparation And Isolation Of Anti-Growth Factor Antibodies

Individuals with strong immune systems are immunized as described in Example 5. After a high titer of anti-growth factor antibody has been achieved the IgG fraction is isolated from blood and is used to passively immunize an individual as described in Example 7 below.

EXAMPLE 7

Passive Immunization

Anti-growth factor antibodies isolated from the species to be passively immunized are administered by intravenous injection as a dosage level of approximately 0.5–50 mg per kg body weight. Dosage and frequency of administration are determined in experimental animals challenged with different tumor types and are adjusted for the specific type of tumor and the particular individual being treated. Important considerations are the aggressiveness of the tumor, propensity for metastatic spread, target organ for metastases, target organ vascularization/availability of tissue access for antibodies, and the stage of tumor development. While it may be true that a standard regimen can be determined that will be universally protective, it may also be that effective therapy will be achieved only with individualized criterion based on tumor type.

EXAMPLE 8

Preparation of Peptide Conjugated Liposomes as Anti-bFGF Vaccine

The following methods and protocols were used for the preparation of anti-growth factor vaccines, particularly anti-bFGF vaccine.

Selection of Peptides

Peptides selected for use in the present invention may comprise whole growth factor proteins, or immunogenic fragments thereof. For this example, an immunogenic peptide was selected from bFGF amino acid sequence.

Groups 8 total groups for the initial immunization
3 liposomes with peptides conjugated
3 liposomes with peptides passively encapsulated
1 liposomes with buffer only, lipids used for conjugated liposomes
1 liposomes with buffer only, lipids used from passively encapsulated
all contain lipid A© 22 µg lipid A/µmole phospholipid Immunization The animal model used for the present example consisted of Balb/CyJ mice. Five mice for each of the eight groups were used.

Liposomes

MLV for conjugated peptides containing mole ratios of: DMPC:DMPG:CHOL:PDS-CHOL:MLA of 9:1:7.4:2:0.02 (10 mol % PDS-CHOL) MLV for passive encapsulation DMPC:DMPG:CHOL:MLA of 9:1:7.5:0.02

Dose

Target doses comprise approximately 10–50/µg peptide plus 100 µg MLA. In sufficient quantities for three injections per mouse for a full course.

Materials 100-ml round-bottom flasks, 24/40 joints, depyrogenate, 35-ml Oakridge tubes. All materials suitably sterilized and autoclaved.

Lipid Aliquotting‡ (per group) with a total of 8 groups)

| Lipid | [Stock] mM | µmol | ml Stock | Mol Ratio |
|---|---|---|---|---|
| DMPC | 90 | 204 | 2.27 | 9 |
| DMPG | 10 | 23 | 2.3 | 1 |
| CHOL | 75 | 170 | 2.27 | 7.4 |
| PDS-CHOL | 20 | 44 | 2.2 | 2 |
| | | | | (20 mnM = 10.26 mg PDS-Chol/ml) |

MLA added at 22 µg/µmol; Lot #4013B from List Biologicals, Inc. ‡ Assuming 100 µg MLA per injection, enough for approximately 50 injections;

Assuming approximately 50% peptide encapsulation using 1.5 mg total peptide and 10 µg per injection, enough for approximately 50 injections.

MLA at 1 mg/vial is dissolved with chloroform:methanol, 1:1, approximately 1 ml/vial and pooled.

Preparation of Pyridyldithio-Cholesterol (PDS-Chol) for Surface Conjugation of Cysteine-Terminal Peptides to Liposomes In order to render relatively nonimmunogenic peptides more immunogenic, surface conjugation of cysteine-terminal peptides derived from VEGF amino acid sequences to liposomes was carried out. PDS-Chol is a thiol-reactive cholesterol analogue that binds free thiols. The peptides possess amino- or carboxyl-terminal thiols that will bind PDS-Chol in an aqueous liposome environment. The peptides are conjugated to multilamellar vesicles (MLV; liposomes) both inside and outside the MLV, thus favoring a depo, or slow release effect for antigen presentation.

The methods used comprise modifications of Carlsson, et al.

Day One 1. 1.772 g (44 mmol) thiocholesterol (Aldrich Chem., #13,611-5) dissolved in 2.6 ml chloroform. 13×100 mm glass screw-cap tube used and composition kept under nitrogen. Composition nearly completely soluble; slightly opalescent with mixing lines.

2. 1.982 g (9.0 mmol) 2', 2' dipyridyldisulfide PDS) (Aldrithiol-2; Aldrich) placed in a 25-ml vaccine vial and 5.6 ml chloroform:glacial acetic acid, 100:1, v:v. added. Stir bar added and composition mixed until dissolved (~2 minutes).

3. Thiocholesterol added dropwise at a rate of approximately 30 drops per minute, to the vigorously mixing PDS. Yellow color evolved.

4. Immediately following thiocholesterol addition, vial purged with nitrogen, sealed, covered with aluminum foil, and mixed overnight at room temperature.

Day Two

5. Solvent evaporated with a stream of nitrogen -with vial in a warm water bath. Dried to a viscous oil. Acetic acid apparent by smell.

6. Composition transferred to a 250 ml round-bottom flask for recrystallization using chloroform to wash out the reaction vial.

7. Composition rotary evaporated to remove chloroform resulting in viscous bright yellow oil. Nitrogen stream reapplied to remove residual solvent.

8. Composition recrystallized by adding 50 ml ~56° C. ethanol. Swirled to dissolve. Sample was completely soluble. Turned to an emulsion upon sitting at room temperature (~20 minutes). Placed on ice for approximately 1 hour. Large white crystals formed.

9. Placed at −20° C. for two days to complete crystallization. Appeared to be a large amount crystallized product. Large white/yellow crystals.

Day 5

10. Recovered by filtration and washing with ice cold (dry ice) ethanol. Desiccated for approximately 4 hours and obtained weight. Structure confirmed by IR and NMR.

11. TLC in hexane:ethyl acetate:diethyl ether:glacial acetic acid, 9:1:1:0.1, v:v.

| | PDA-Chol | PDS | Thio-cholesterol |
|---|---|---|---|
| Rf's | 0.74 | 0.22 | 0.92 |

Day 18

12. Second round of recrystallization using 100 ml ethanol at 63° C. Sit at room temperature for approximately 2 hours and then placed at −20° C. for 2 days.

TLC RF'S

Solvent System: Hexane:ehtyl acetat:diethyl ether:glacial acetic acid, 9:1:1:0.1, v:v

|  | PDS-CHOL | PDS | Thio-Cholesterol |
|---|---|---|---|
| TLC | 0.74 | 0.22 | 0.92 |
| TLC Previous Synth. | 0.63 | 0.14 | 0.97 |
| Analytical Plates: 1 mm Thick | 0.84 | 0.31 | 0.97 |
| Prep-TLC | 0.55 | n/a | n/a |
| Purity Check TLC Analytical Plates | 0.63 | 0.18 | |

Stock Solution: Made to 20 mM @ 512.77=10.26 mg/ml chloroform.

Weight vs. Absorbance

Assay is based on the DTT-release of 2-thiopyridone, which absorbs strongly at 343 nm. Extinction coefficient is 7.0/mM at 343 nm.
1. 3 separate samples of PDS-Cholesterol weighed out in 13×100 tubes.
2. 2.5 mM (1.282 gm/ml) stocks in ethanol for PDS-Chol and 2-PDS (2-Aldrithiol-2™; Aldrich).
3. PDS-chol diluted in ethanol and 2-PDS in 0.1M sodium bicarbonate to 0.125 mM. Molecular weight PDS-Chol=512.77.
4. 50 mM (7.72 mg/ml) dithiothreitol in 0.1M sodium bicarbonate prepared.

Results

Analysis using functional group-specific sprays: Sterol Spray: Ferric chloride spray: specific for sterols: positive for suspected PDS-cholesterol and thiocholesterol, negative for 2-PDS. Iodine vapor: Showed 90–95% purity (estimated)

Surface Conjugation of Peptides: Method (Use biosafety cabinet for manipulations)

Day 1
1. Aliquotted lipids into depyrogenated 100-ml round bottom flasks, in the following order; lipid A in 1:1 chloroform:methanol, DMPC, DMPG, and cholesterol.
2. Rotary evaporated to remove bulk solvent. Bath was 42° C. Flask rotation was set at 160 rpm. Started at ~22 mm Hg vacuum until bulk solvent evaporated and then increased vacuum to 25 mm Hg and ran for 5 minutes. Blew nitrogen into flask and stoppered until flasks were ready for desiccation.
3. Covered flask openings with filter paper and desiccated under vacuum for 3 hours.
4. While lipid was desiccating, deoxygenated sterile water by nitrogen bubbling through a sterile plugged 5 ml pipette for 20 minutes. Also prepared 10 ml 10 mM acetic acid and filter sterilize. Stock HOAc is 17.5 N. Added 20 microliters of stock HOAc to 35 ml water to give 10 mM. pH was 3.4. Nitrogen bubbled to deoxygenate and filter sterilized with a 0.22 micron syringe filter.
5. Completely dissolved peptides to 5 mg/ml sterile 10 mM acetic acid. Peptide information is listed in the table below:

| Peptide Expt. # | Manuf. # | Physical State |
|---|---|---|
| BFGF | Research Genetics, Huntsville, Alabama | Fluffy White Powder |

Solubilities

The white powder dissolved completely; practically immediately.
6. Added 0.2 ml the 5 mg/ml peptide solution (1 mg) to 6.4 ml deoxygenated DIW and mixed gently. This is the peptide hydration solution.
7. Added the peptide hydration solution to the desiccated lipid. Purged flask with nitrogen and glass-stoppered and sealed with parafilm.
8. Bath sonicated to resuspend the lipid. A milky suspension resulted. Vortexed briefly.
9. Placed on orbital shaker, covered with foil and rotated overnight at setting 3.25 at room temperature.

Day 2

10. Transferred the preps to a sterile 20 ml vaccine vials and lyophilized for 3 days.

Day 3

11. Prepared 0.1 M citrate/phosphate buffer, pH 5.6 (C/P buffer): Dissolve 1.921 g citric acid in 100 ml DIW ("A"); dissolve 5.37 g dibasic & odium phosphate-7-hydrate in 100 ml DIW (CC B"); Mix 21 ml "A" and 29 ml "B" and add 50 ml DIW. Deoxygenate by nitrogen bubbling and filter sterilize.
12. Pre-form the liposomes by adding 2.135 ml sterile C/P buffer, purging vial with nitrogen and vortexing vigorously for 1–2 minutes. Suspension was relatively even. Lyophilization may be the limiting factor, due to large ratio of fluid:vial capacity.
13. Dissolved completely each peptide to 10 mg/ml in sterile, degassed 10 mM acetic acid. Powder was immediately soluble, solids dissolved completely in about 1 minute with swirling.
14. Added 0.2 ml the 10 mg/ml peptide/HOAc solution (2 mg) to the pre-formed vesicles, purged the vial with nitrogen, seal, and cover with foil.
15. Mixed on orbital shaker at setting 6 overnight at room temperature.

Day 4

16. First spin: Washed out vial sequentially with two 1-ml aliquots of PBS and then 0.5 ml PBS for a total of 2.5 ml of sterile PBS to the lipid. 1-ml plastic pipettes are best to use for transferring. Total volume of prep wag 5 ml. Measured a lipid pellet by volume and found it to be 1.5 ml. Used sterile PBS and autoclaved Qakridge tubes.
17. Centrifuged in Sorvall high-speed in SS-34 rotor at 15,000 rpm, 40° C., 30 minutes.
18. Carefully pipetted off supernatant and stored frown. Tubes labeled 1st Spin. Total volume of 5 ml; lipid volume of 1.5 ml; so ~3.5 ml is aqueous and should be used for the calculation, using each peptide stock as the standard in a BCA assay.
19. Second Spin: Added ~5 ml PBS to pellet and vortexed to completely re-suspend the pellet. Added a total of 30 ml PBS and inverted to mix.
20. Centrifuged in Sorvall high-speed in SS-34 rotor at 15,000 rpm, 4° C., 30 minutes.
21. Decanted supernatant into 50-ml tubes labeled second spin and stored frozen. The control pellets were looser in both groups. Peptide pellets were tight and supernatants clear.
22. Added ~1 ml PBS to pellet and carefully resuspended pellet to an even suspension. Transferred to a 5-ml sterile snap-cap tube. Used enough PBS to make the total suspension 5 ml.
23. Assay for phosphorous; for incorporation by BCA (use each peptide as its own standard). Use 10 mg/ml frozen peptide stocks.

Injections
  Optimal=100 μl i.p. containing 100 pg Lipid A and 10 μg peptide

Method for Simple encapsulation of peptides: Day 1
1. Aliquotted lipids into depyrogenated 100-ml round bottom flasks, in the following order: lipid A in 1:1 chloroform:methanol, DMPC, DMPG, and cholesterol.
2. Rotary evaporated to remove bulk solvent. Start at ~22 mm Hg vacuum until bulk solvent evaporates and then increase vacuum to 25 mm Hg and run for 5 minutes.
3. Desiccated under vacuum for at 2 hours.
4. Hydrated lipid as follows; Added 4.5 ml sterile water to lipid and bath sonicated to suspend lipid. A relatively even suspension resulted. Let stand at room temperature for 2 hours.
5. Transferred to 10-ml vaccine vials. Washed out the rotary flask with successive 1 ml aliquots of sterile water. Sealed vials with sterile butyl-type rubber vaccine vial septa and parafilm.
6. Vials were frozen on dry ice for 30 minutes.
7. #20 sterile hypodermic needles were placed through the septa to allow air flow for lyophilization.
8. Vials were placed in lyophilizer. 2 days should be sufficient to lyophilize the lipid.

Day 2
9. Concentrated peptide solutions (10 mg/ml) in 10 mM HOAc prepared. 0.5 ml necessary for 5 mg total peptide Once dissolved, peptide solution diluted into 2 ml sterile, room temperature PBS.
10. The 4.5 ml peptide solutions then added to the lyophilized lipid and the vials vortexed vigorously for 2 minutes. This gave a final concentration with respect to phospholipid of ~100 mM.
11. Vials were placed at 4° C. for ~24 hours to allow encapsulation.

Day 3
12. Lipid transferred to 35-ml sterile Oakridge tubes for centrifugation. Used 1-ml pipette for the transfer. Used two 1-ml aliquots of cold PBS to wash out vials. Total volume of the prep was 7 mls. Pellet volume was measured to be ~1.5 ml.
13. Centrifuged in Sorvall High-speed in SS-34 rotor for 30 minutes at 15,000 rpm, 4° C.
14. Supernatant pipetted off and stored frozen as 1st Spin.
15. ~5 ml PBS added to pellet and vortexed to resuspend pellet evenly. PBS added to a total of 30 ml and centrifuged as above.
16. Pellet resuspended with PBS and transferred to 5-ml snap-cap tubes to a total of 5 mls.
17. Assay for phosphorous and peptide encapsulation.

EXAMPLE 9

In Vivo Studies for Demonstrating the Effect of bFGF Heparin Binding Domain Peptide Vaccination Two peptides from the functional domain of the bFGF molecule were analyzed for the ability to block bFGF stimulated endothelial cell proliferation in vivo. Peptide A is a 45 amino acid peptide corresponding to the heparin-binding domain of bFGF with the sequence: YCKNGGF-FLRIHPDGRVDGVREKSDPHIKLQLQAEERGV VSIKGV (SEQ ID NO: 1).

Peptide B is a 21 amino acid peptide and corresponds to the receptor binding domain with the sequence SNNYN-TYRSRKYSSWYVALKR (SEQ ID NO: 2).

Both peptides A and B were incorporated into lipid A containing liposomes and used separately in a vaccination protocol. Peptides were conjugated to liposomes according to the methods and protocols described above in Example 8. Mice were immunized and boosted twice, bled and pooled serum analyzed for anti-peptide antibody titer and crossreactivity to bFGF by ELISA.

Figure 4:
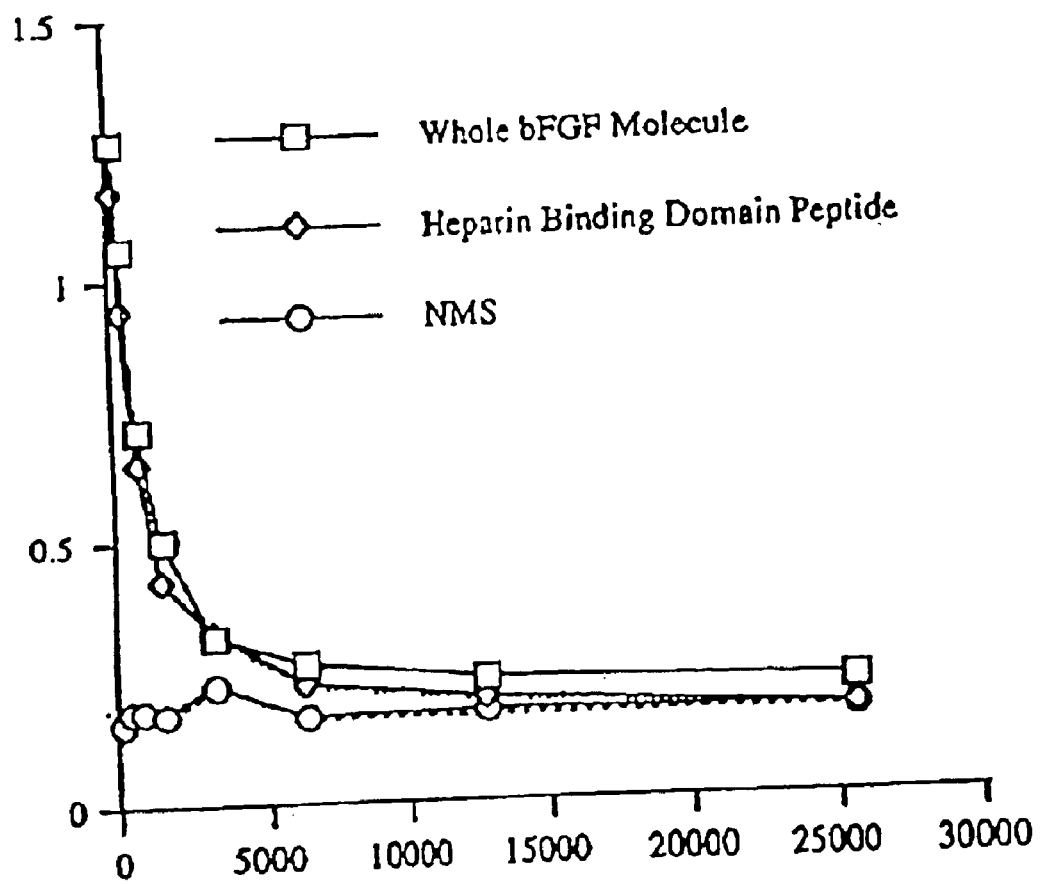
FIG. 4 is a graph showing the reactivity of serum from mice vaccinated with the heparin binding domain peptide of bFGF against with whole bFGF (open square), heparin binding domain peptide bFGF (open diamond), and in comparison to normal mouse serum (NMS) (open circle).
Figure 5:
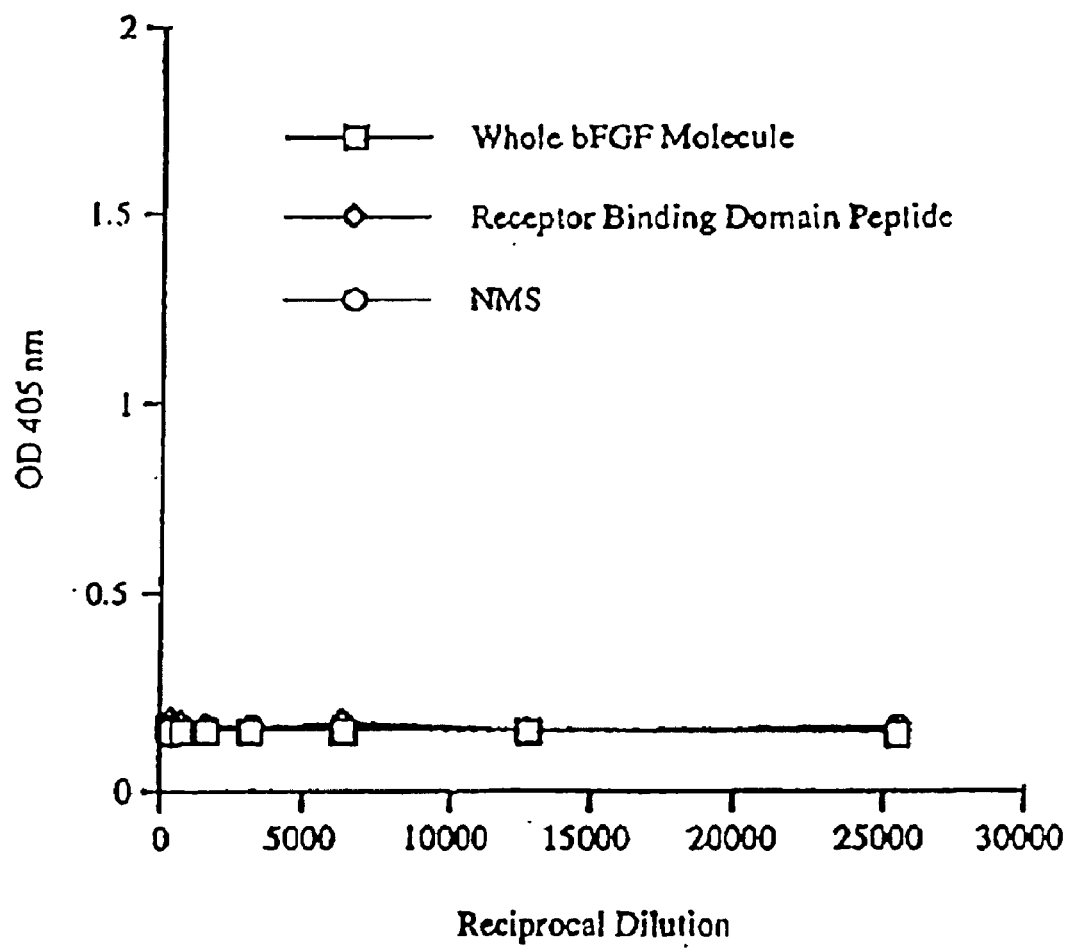
FIG. 5 is a graph showing the reactivity of serum from mice vaccinated with the receptor binding domain peptide of bFGF with whole bFGF (open square), receptor binding domain peptide (open diamond), and NMS (open circle).

The comparison of titers and crossreactivity for serum from mice vaccinated with whole bFGF or with the liposomal heparin binding domain peptide of bFGF vaccine is shown in FIG. 4 and a comparison of the titers and cross-reactivity for serum from mice vaccinated with whole bFGF or the liposomal receptor binding domain peptide of bFGF vaccine is shown in FIG. 5.

Figure 6:
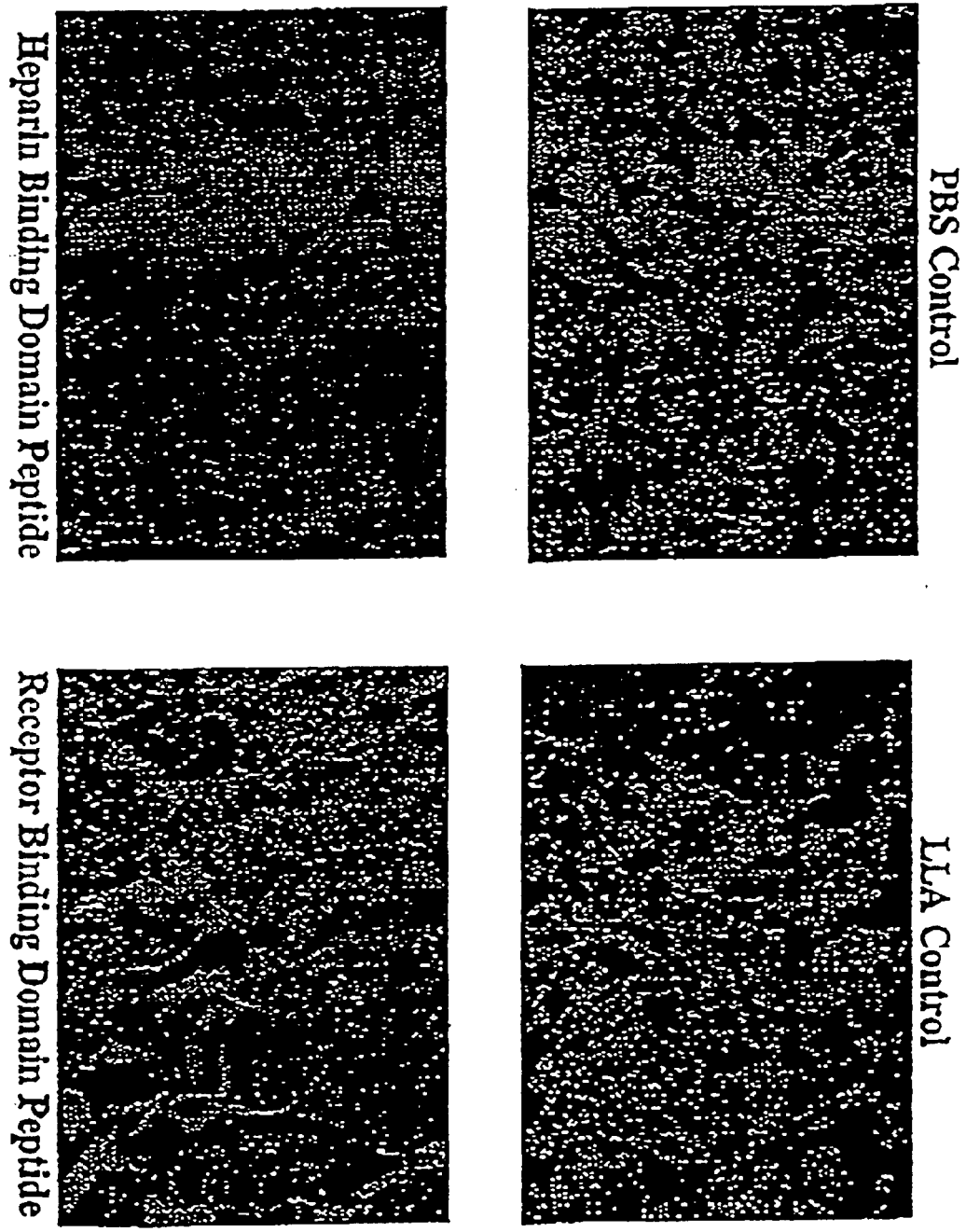
FIG. 6 shows histological analysis of gelatin sponges removed from mice vaccinated with PBS controls, LLA controls, heparin binding domain peptide of bFGF and receptor binding domain peptide of bFGF. As further described in Example 9, in order to determine if generation of antibody to the bFGF molecule has an effect on bFGF-induced vascularization, gelatin sponges containing recombinant human bFGF were implanted onto the left lobe of the liver of mice following vaccination with the liposomal lipid A controls, liposomes containing the heparin binding domain peptide, liposome containing the receptor binding domain peptide, or PBS.

Following the vaccination protocol, mice were challenged with bFGF impregnated sponges and neovascularization assessed after 14 days, the results are shown in FIG. 6.

In order to determine if generation of antibody to the bFGF molecule has an effect on bFGF-induced vascularization, gelatin sponges containing recombinant human bFGF were implanted onto the left lobe of the liver of mice following vaccination with the liposomal lipid A controls, liposomes containing the heparin binding domain peptide, liposome containing the receptor binding domain peptide, or PBS. Fourteen days following implantation, the sponges were removed. Vascularity and leukocyte infiltration were assessed histologically. Well defined blood vessels containing red blood cells were evident in sponges removed from mice vaccinated with control preparations (liposomal lipid A and PBS). In addition, there was an abundant amount of cellular infiltration, consisting of white blood cells and fibroblasts. Sponges removed from mice vaccinated with the receptor binding domain looked similar to the controls. In contrast, histological analysis of sponges removed from mice vaccinated with the heparin binding domain peptide revealed lack of cellular infiltration and neovascularization induced by bFGF. Although red blood cells were present in the histological sections of the sponge taken from mice vaccinated with the heparin binding domain peptide, they lacked well defined structures surrounding them.

Inhibition of B16-BL6 induced Angiogenesis and Tumor Growth in Hepatic Sponge Implants In order to determine if vaccination could inhibit the angiogenesis induced by a tumor, gelatin sponges were implanted containing B16-BL6 melanoma cells onto the liver of mice following vaccination with control liposomes (liposomal lipid A), liposomes linked to the heparin binding domain peptide, liposomes linked to the receptor binding domain peptide, or PBS. Fourteen days following implantation, the sponges are removed and examined histologically. Sponges removed from mice vaccinated with liposomal lipid A and PBS contained viable and proliferating B16BL6 tumor cells. In addition, neovascularization into the sponge was abundant. A similar effect was seen in sponges removed from mice vaccinated with liposomes containing the receptor binding domain. Vaccination with the heparin binding domain peptide blocked neovascularization and caused ablation of tumor growth and development in the sponge. Similar to findings from sponges containing bFGF, there was a tremendous amount of red blood cells lacking defined structures surrounding them.

Figure 7:
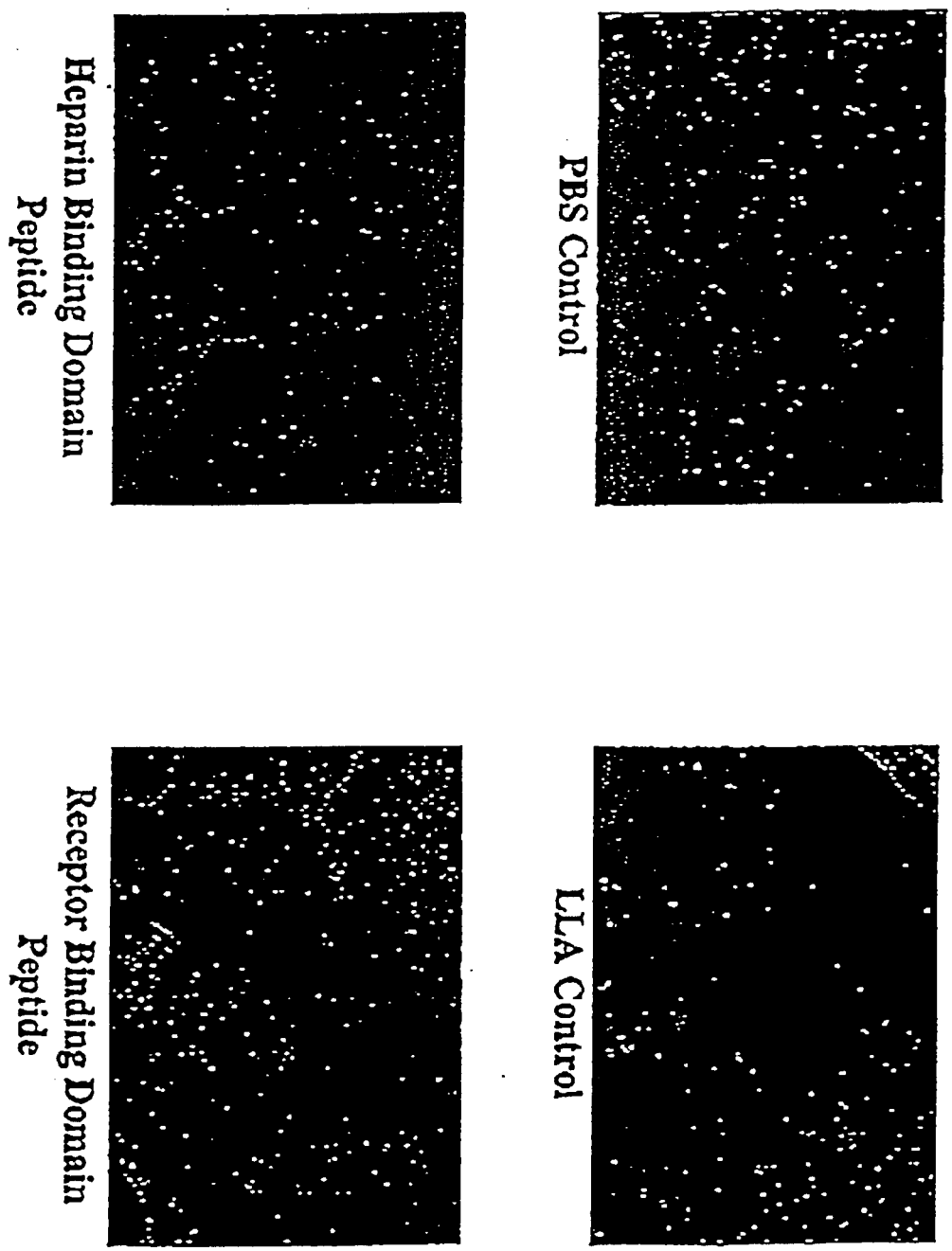
FIG. 7 shows histological analysis of gelatin sponges removed from mice vaccinated with PBS controls, LLA controls, heparin binding domain peptide of bFGF and receptor binding domain peptide of bFGF. As further described in Example 9, in order to determine if vaccination could inhibit angiogenesis induced by a tumor, gelatin sponges containing B16-BL6 melanoma cells were implanted onto the liver of mice following vaccination with control liposomes (liposomal lipid A), liposomes linked to the heparin binding domain peptide, liposomes linked to the receptor binding domain peptide, or PBS.
Figure 8:
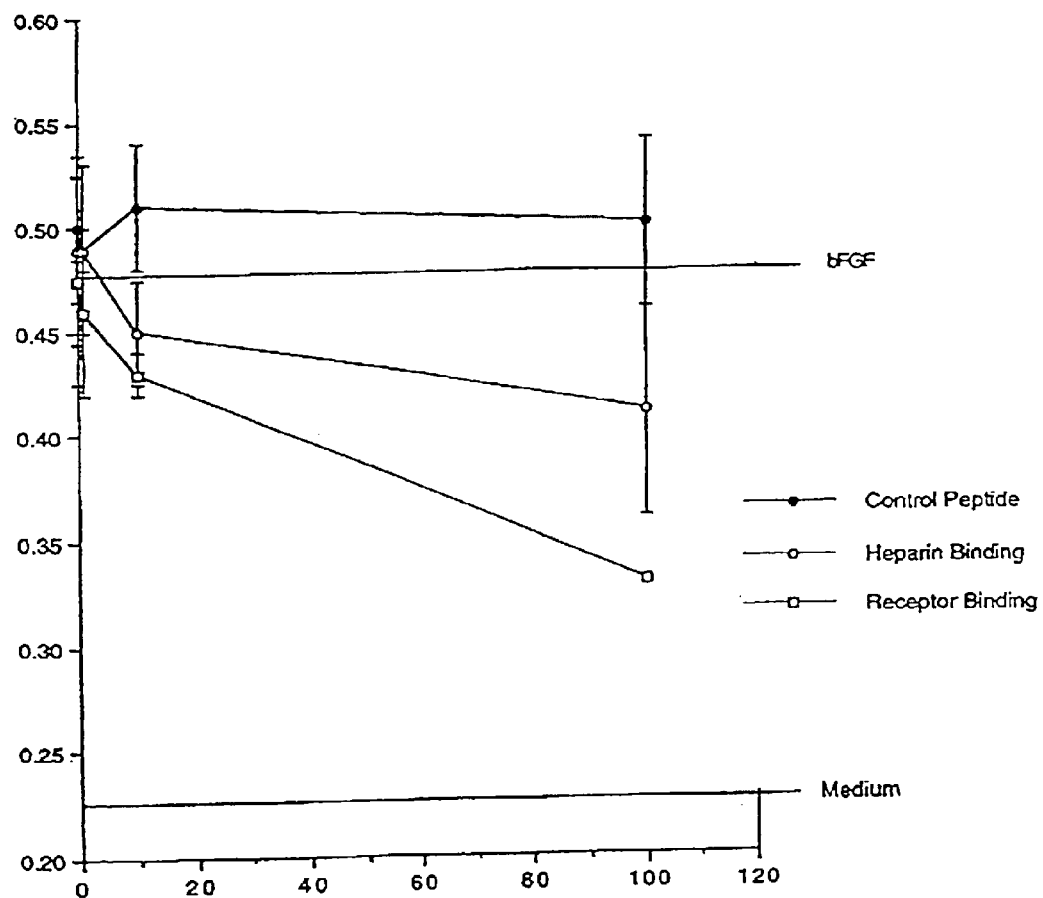
FIG. 8 shows bFGF stimulated proliferation of HUVEC in the presence of bFGF peptides: control peptide (closed circle), heparin binding domain peptide of bFGF (open circle), and receptor binding domain peptide of bFGF (open square).
Figure 9:
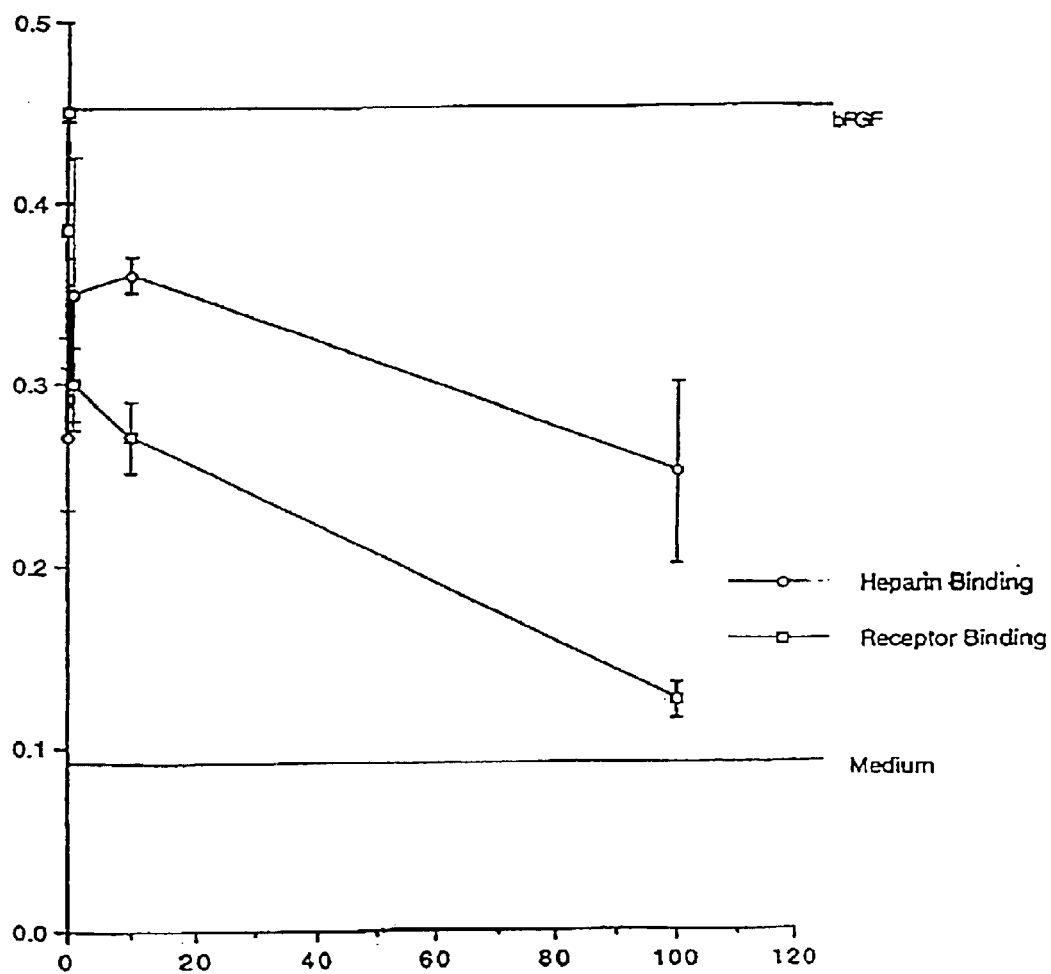
FIG. 9 shows reproducibility of the effect shown in FIG. 8: bFGF stimulated proliferation of HUVEC in the presence of bFGF peptides: heparin binding domain peptide of bFGF (open circle), and receptor binding domain peptide of bFGF (open square).

Results of these experiments are provided in FIGS. 6 and 7.

EXAMPLE 10

In Vivo Studies for Demonstrating the Effect of bFGF Heparin Binding Domain Peptide on Lung Metastases on Mice In order to test the effectiveness of bFGF peptide from the heparin-binding domain for inhibiting cancer, groups of 10 mice were vaccinated, boosted, and challenged with B16B16 murine melanoma by the intravenous route. Peptides A and B as described in Example 9, were conjugated to liposomes according to the methods and protocols described above and particularly in Example 8.

Figure 1:
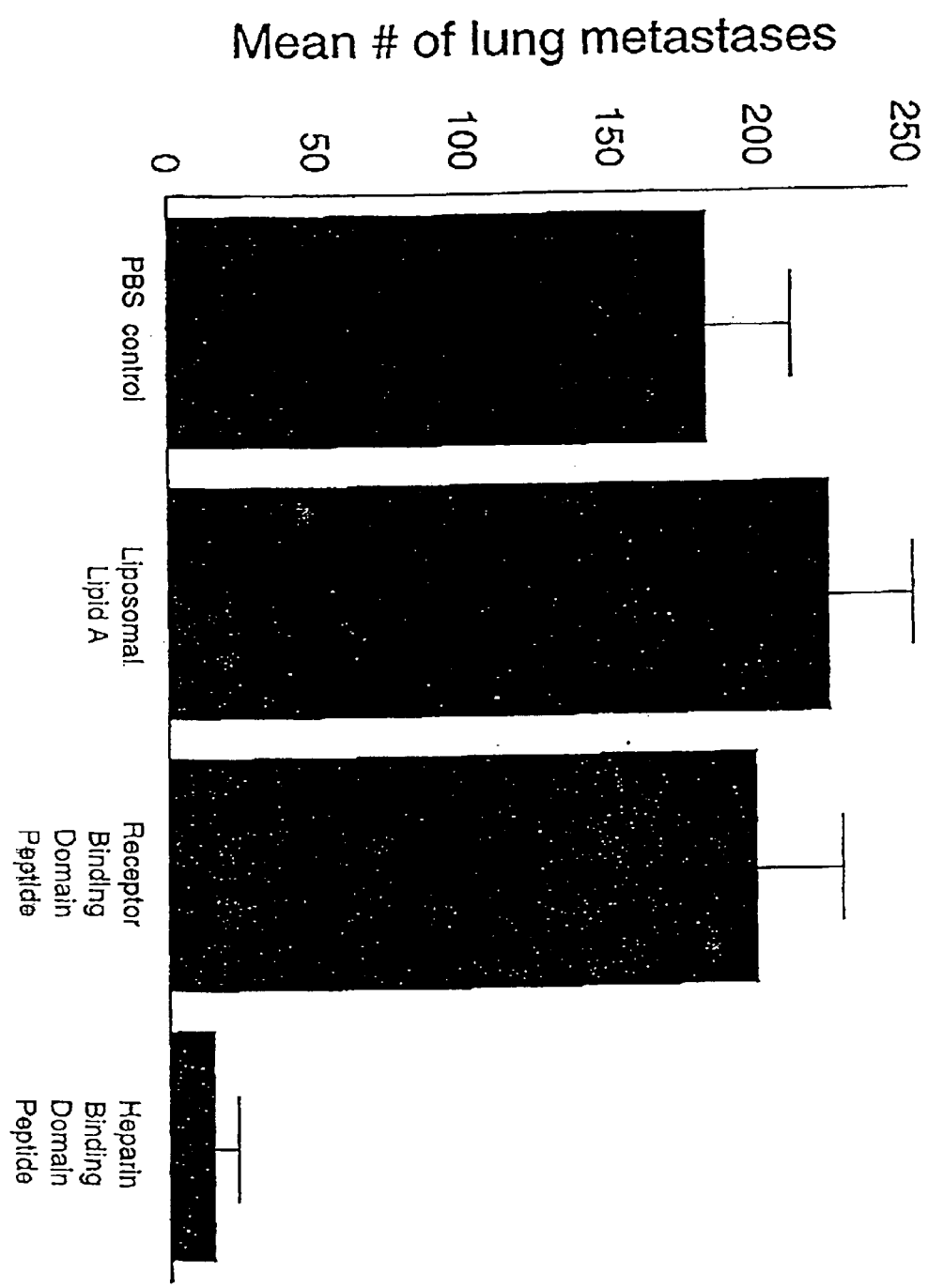
FIG. 1 is a bar graph showing the mean number of lung metastases in mice challenged with B16BL6 metastatic melanoma for four different groups of mice: unvaccinated mice (PBS controls), mice vaccinated with empty liposomes (Liposomal Lipid A), mice vaccinated with a peptide from the receptor binding domain of bFGF conjugated to liposomes, and mice vaccinated with bFGF peptide from the heparin-binding domain conjugated to liposomes
Figure 2:
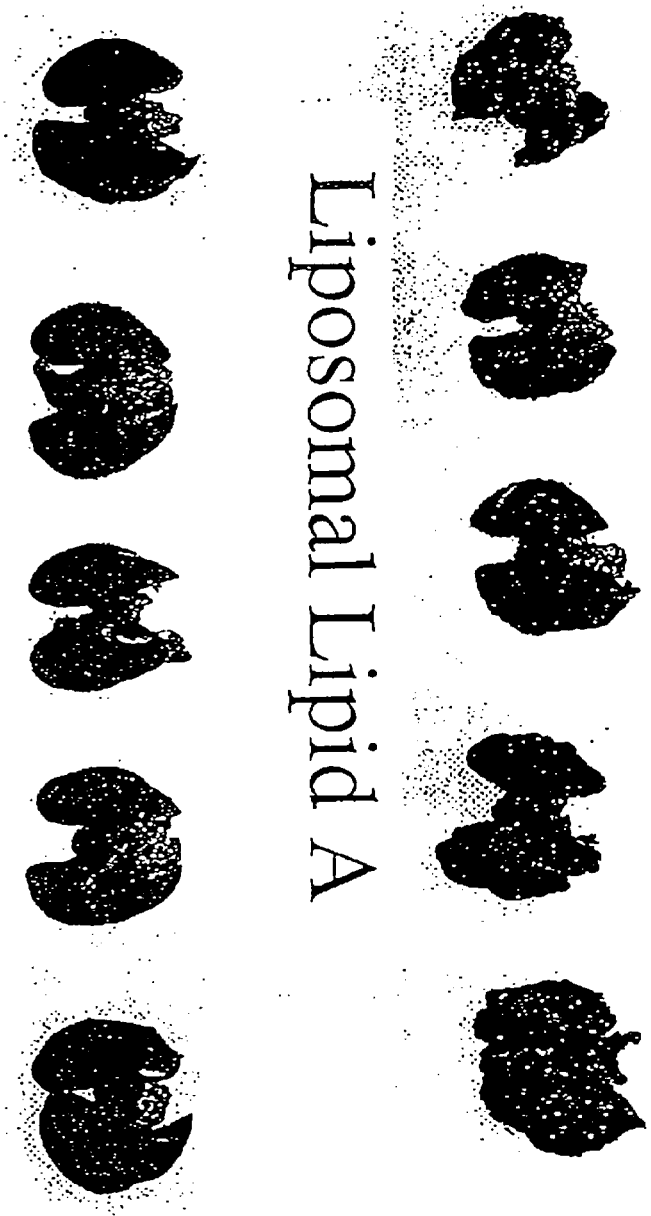
FIG. 2 is a photograph comparing the differences in surface B16BL6 metastases in the lungs from mice treated with liposomal lipid A ((control) top row) and mice treated with heparin-binding domain peptide (bottom row).
Figure 3:
FIG. 3 is a photograph comparing the effect of heparin-binding domain peptide vaccination on mouse lung to the effect of control vaccination on pulmonary B16BL6 growth and development.
Figure 3:
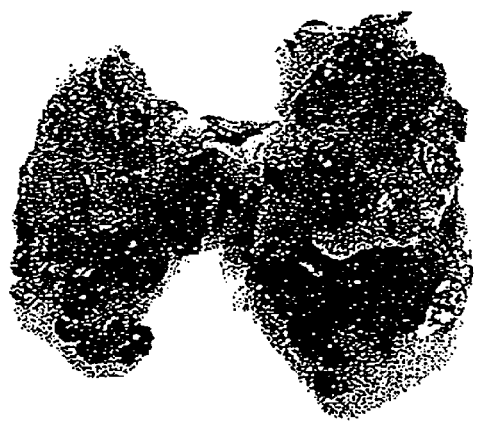

Fourteen days after the mice were vaccinated, boosted, and challenged with B16B16 murine melanoma, the animals were sacrificed and the lungs were removed and numbers of melanotic tumor nodules on the surface were counted. FIG. 1 shows the mean number of lung metastases in (a) mice vaccinated with bFGF peptide from the heparin-binding domain conjugated to liposomes, (b) mice vaccinated with a peptide from the receptor binding domain conjugated to liposomes, (c) mice vaccinated with empty liposomes, and (d) unvaccinated mice (PBS controls). FIG. 2 shows the differences in surface metastases in the lungs from the control group (liposomal lipid A, top row) and the lungs from the vaccinated group (heparin-binding domain peptide, bottom row).

As demonstrated by the results of this experiment, and shown in FIG. 1, the administration of compositions comprising the heparin binding domain peptide of bFGF significantly reduces the mean number of lung metastases and is therefore an effective anti-tumor composition.

EXAMPLE 11

Effect of Growth Factor and Liposome Vaccine Compositions on Tumor Volume and Size Compositions comprising bFGF-liposomes were administered to tumor bearing mice in order to monitor the effect of such compositions on tumor size.

Materials and Methods

A. Preparation of Vaccines Comprising Liposomes The liposomes used in these studies were made according to the method of Verma et al. Infect Immun 60(6):2438–2444 (1992). The vaccine was prepared by combining lipids, dimyristoylphosphatidylcholine (DMPC), dimyristoylphosphatidylglycerol (DMPG), cholesterol (CHOL), and Lipid A at a mole ratio of DMPC:DMPG:CHOL:LA, 9:1:7.5:1 (mol:mol) in pyrogen-free rotary evaporator flasks. Flasks were desiccated at least 2 hours under high vacuum. The lipids were hydrated in sterile water for 2 hours at room temperature. The hydration concentration used was 50 mM with respect to phospholipid. The samples were then lyophilized. Recombinant human bFGF was encapsulated into the liposomes by dissolving in PBS and combining with the lyophilized lipid. The mixture was vortexed vigorously to ensure resuspension of lipid and incubated at 4° C. for 2 days. The amount of vaccine injected was determined by the amount of protein desired per dose. For mice, and perhaps for man, the adjuvant lipid A is generally preferred for a vigorous response. For these studies, the dose of adjuvant was 200 µg per injection per µmol total phospholipid and antigen dose 10 µg bFGF per injection. Concentration of liposomes is given as total phospholipid, i.e., total DMPG and DMPC; liposome (vaccine) final concentration was 10 mM phospholipid. Maximum efficacious doses may vary and studies to address this are ongoing.

B. Immunization Schedule
C57BL/6J or BALB/cByJ mice, 6–8 weeks old, were immunized by intraperitoneal injection of liposomes containing bFGF at day 0, day 14, and day 21. Serum was collected at day 0, day 14, day 21, and day 35. Serum was analyzed for anti-bFGF activity by ELISA. Control groups of mice included uninjected mice that had been bled for titers and mice inoculated with liposomes alone and similarly bled for anti-bFGF titers.

C. Analysis of Vaccine Efficacy
  a. Antisera from vaccinated mice was analyzed for anti-bFGF activity by ELISA assay.
  b. Two tumor models were used for analysis of anti-tumor therapeutics: B16F10, a highly tumorigenic melanoma that induces macroscopic lung tumors 14 days after intravenous inoculation of $10^6$ cells in C57BL/6J mice; and Lewis lung carcinoma-low metastatic (LLC-LM) developed by M. O'Reilly at Children's Hospital. Further, efficacy of the vaccination protocol as an anti-cancer therapy was evaluated in both allogeneic and syngeneic systems; the former being highly immunogenic tumors, the latter being non-immunogenic.

Groups of mice that were vaccinated, unvaccinated, and control liposome (no bFGF) vaccinated, were challenged with B16F10 intravenously and analyzed at 14 days for lung tumors. Numbers of tumors visible by stereomicroscopy at 4× magnification were determined for each group.

Efficacy of the anti-bFGF vaccine was analyzed on both primary tumor growth and subsequent development of metastatic disease using the LLC-LM model developed by M. O'Reilly. Fourteen days after the last boost, mice were challenged with $10^6$ LLC-LM (taken directly from tumor bearing mice). Tumor volume was measured at 14–21 days after inoculation and compared between the groups. At that time (14–21 days after tumor inoculation) tumors were resected from half of the group, the other half underwent sham operation. Fourteen days following surgery mice were sacrificed, lungs excised and weighed, and lung metastases counted using a stereomicroscope.

Results

Figure 10:
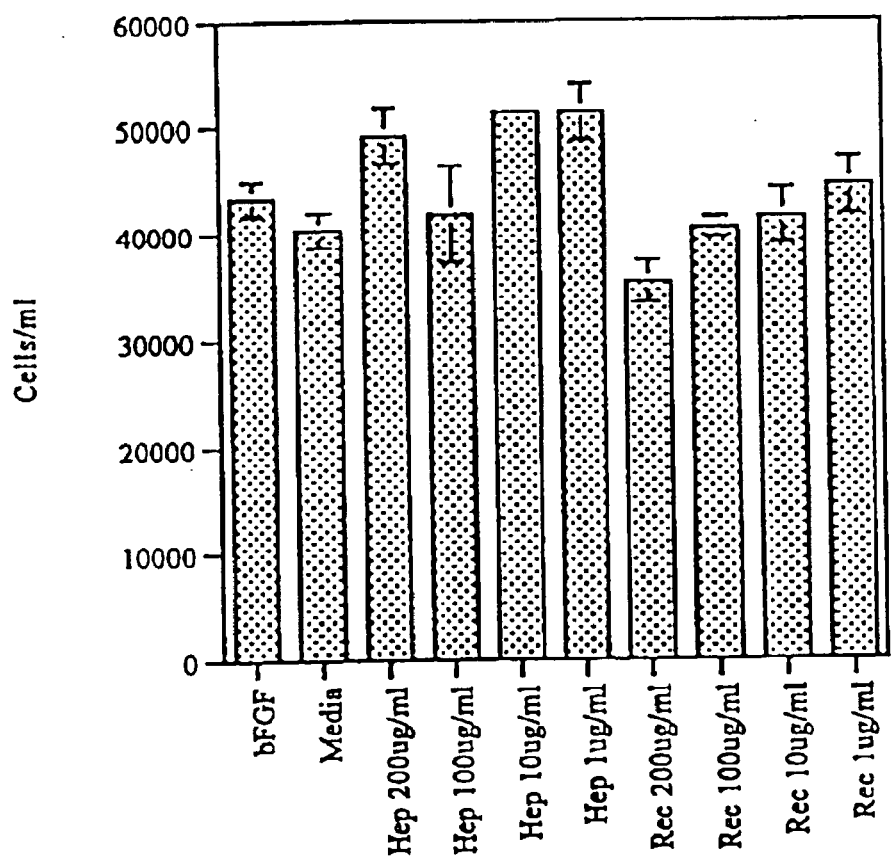
FIG. 10 is a bar graph demonstrating the comparative effects of the heparin binding domain peptide of bFGF or receptor binding domain peptide of bFGF on the growth of B16BL6 tumor cells in vitro.
Figure 13:
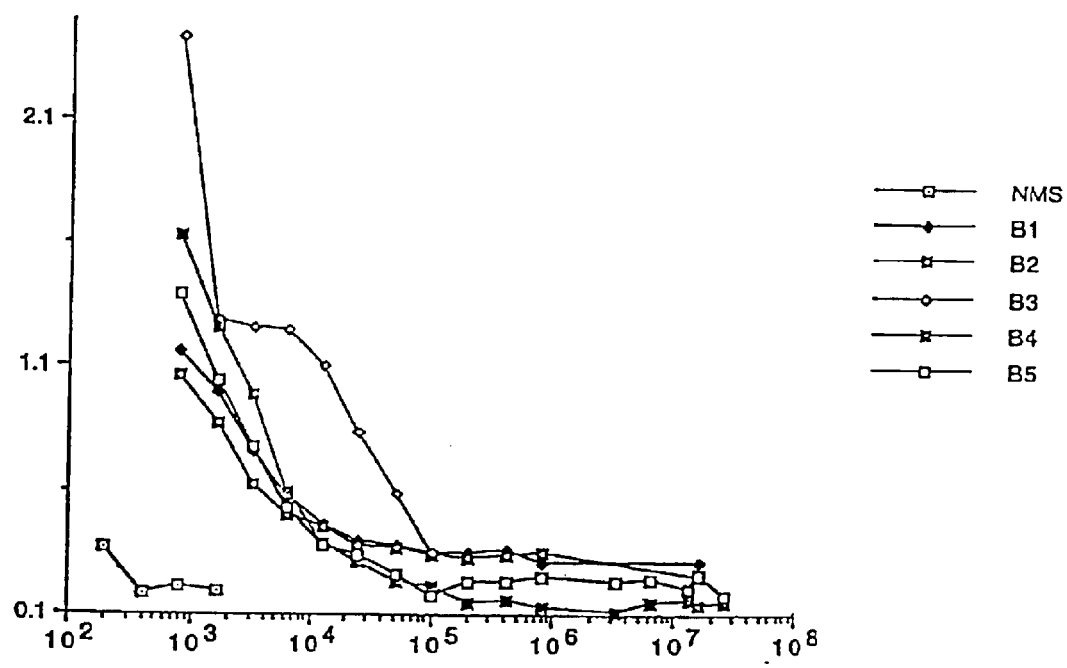
FIG. 13 is a graph showing anti-bFGF titers in serum from individual mice vaccinated with bFGF-liposomes. As discussed in Example 11, C57BI/6J mice were vaccinated with liposomes containing bFGF according to the protocol outlined in the methods section. Serum from individual mice labeled B1–B5 was collected on day 35, serially diluted, and analyzed for reactivity to whole bFGF by measuring absorbance in an ELISA assay. Reactivity of serum from mice vaccinated with the liposome control was not different from the NMS. Data shown corresponds to methods and protocols of Example 11 as follows: NMS (open square with dot), mouse 1 (solid diamond), mouse 2 (solid square with white dot), mouse 3 (open diamond); mouse 4 (solid square), and mouse 5, (open square).

Preliminary data derived from bFGF-liposome-vaccinated and control liposome-vaccinated BALB/cByJ mice indicated that bFGF vaccine stimulated an anti-bFGF antibody response. Anti-bFGF titers ranged from 1:12,800 to 1:30,000 for vaccinated BALB/cByJ mice in two separate experiments (FIGS. 10A and 10B). Similarly, C57BL/6J mice responded to vaccination with anti-bFGF titers of 1:10,000 to 1:50,000 measured in individual mice (FIG. 13).

Figure 14:
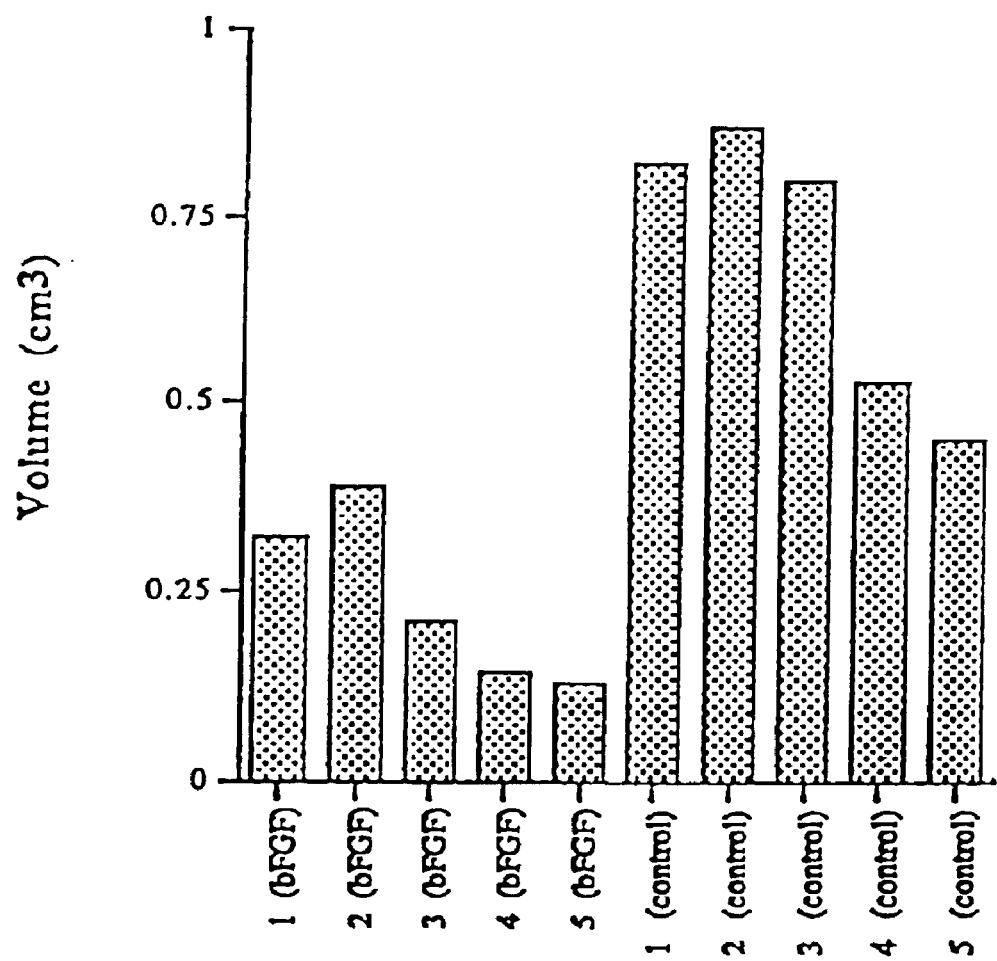
FIG. 14 is a graph showing primary tumor size in mice vaccinated with bFGF or control liposomes 14 days after challenge. As discussed in Example 11, BALB/cByJ mice were vaccinated with liposomes containing bFGF (bFGF) or liposomes without bFGF (control) according to the protocol outlined in the methods section. On day 35 mice were challenged with $1 \times 10^6$ LLC-LM subcutaneously in the back. The data shown represent tumor volumes measured 14 days after challenge for each of 5 mice in each vaccination group.

Immune BALB/cByJ mice were challenged with LLC-LM (allogeneic system) and primary tumor development assessed over a 21 day period. The mean tumor volume in control liposome-vaccinated mice was 830 mm$^3$, compared with 290 mm$^3$ in similarly challenged bFGF-liposome-vaccinated mice on day 14 following tumor implantation (FIG. 14). In this experiment the T/C=0.35 (7/c refers to the number of lung nodules in the vaccinated group divided by the number of nodules in the control vaccine(liposomes only, no peptides)); a 65% reduction in tumor size relative to the controls.

Figure 15:
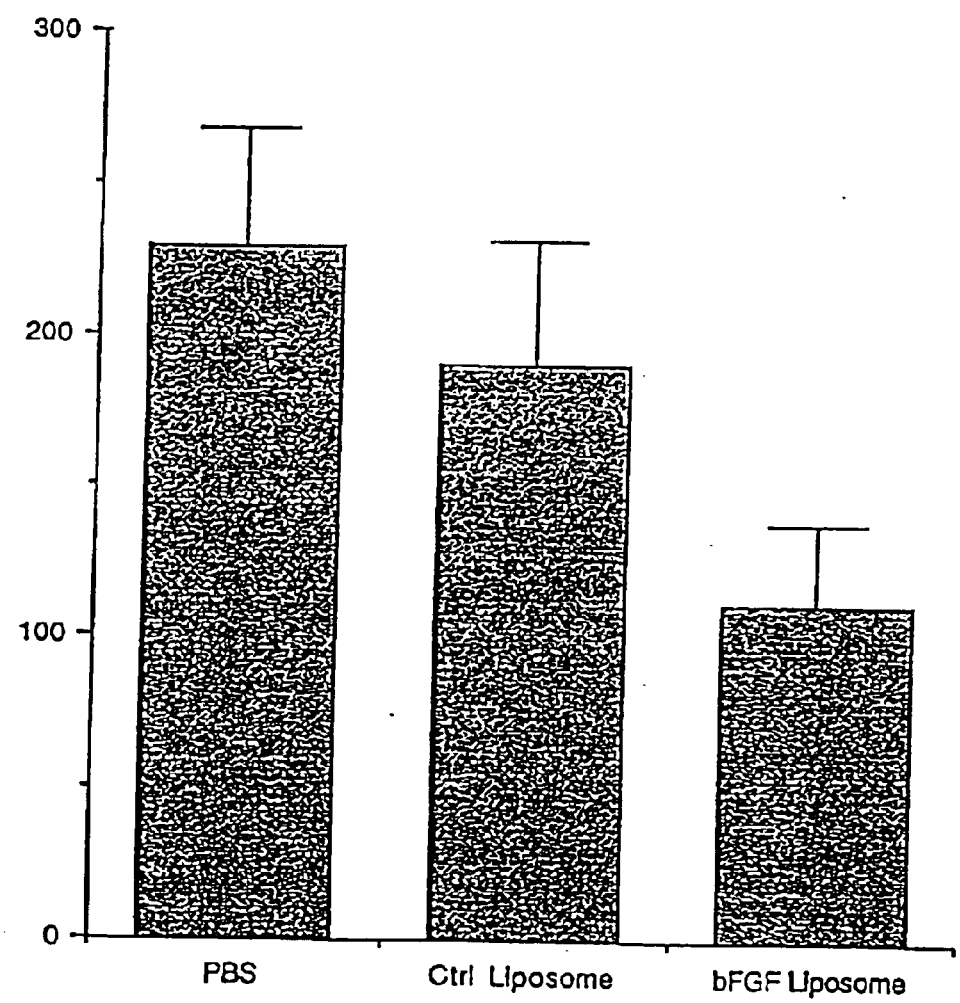
FIG. 15 is a bar graph showing primary tumor size in mice vaccinated with bFGF or control liposomes 14 days after challenge. As discussed in Example 11, groups of 5 BALB/cByJ mice were vaccinated with liposomes containing bFGF (bFGF Liposome), nothing (Ctrl Liposome), or treated with PBS (PBS), according to the protocol outlined in the methods section. On day 35 mice were challenged with $1 \times 10^6$ LLC-LM subcutaneously in the back. The data shown is the mean tumor volume±1S.D. of the mean measured 14 days after challenge for each of the three vaccination groups.

In a second experiment with LLC-LM in vaccinated and unvaccinated BALB/cByJ mice, the mean tumor volume in control liposome-vaccinated mice was 229 mm$^3$, compared with 111 mm$^3$ in similarly challenged bFGF-liposome-vaccinated mice on day 14 following tumor implantation (FIG. 15). For this experiment the T/C=0.48; a 52% reduction in tumor size.

The BALB/cByJ mouse is allogeneic for the LLC-LM and tumor sizes in all groups were smaller than those observed in syngeneic C57BL/6J mice. Thus, the next set of experiments were performed with vaccinated C57BL/6J mice challenged with: (a) LLC-LM (primary tumor development and metastatic disease assessed); or (b) B16F10 (numbers of metastases determined); both syngeneic models.

As shown in FIG. 13, C57BL/6J mice responded to vaccination with production of bFGF antibodies. To assess the protective efficacy of the induced bFGF antibodies in a syngeneic tumor system, vaccinated mice were challenged with LLC-LM and primary tumor growth and subsequent metastatic disease was assessed. In this syngeneic system vaccination and the resulting circulating bFGF antibodies response to bFGF did not alter the growth of primary. LLC-LM in C57BL/6J mice.

Vaccinated mice underwent surgical resection of the primary tumor to assess the extent of metastatic disease following removal of the primary tumor. In the LLC-LM model of metastatic disease, removal of the primary tumor leads to rapid growth of metastatic tumor in the lungs with a concomitant increase in lung weight. Vaccination had no effect on development of metastases following primary tumor removal, as assessed by the lung weight measured 14 days after primary tumor removal.

Finally, C57BL/6J mice were vaccinated and challenged with B16F10 by intravenous route to assess vaccine efficacy in a syngeneic model of experimental metastasis. Anti-bFGF titers in vaccinated nice were 1:16,000 but numbers of B16F10 metastases in the lungs of bFGF-liposome vaccinated mice were not different from the numbers of metastases in the lungs of mice vaccinated with the control liposome preparation or control mice (inoculated with PBS).

Conclusion

The data generated by the present experiment demonstrate that a vaccine composition comprising a growth factor, particularly fibroblast growth factor, can be effectively used to reduce or prevent a cancerous tumor, particularly an allogeneic cancerous tumor or one that is highly immunogenic. As shown in both parts of the experiment, mice which were immunized with fibroblast growth factor incorporated into a liposome and challenged with an allogeneic tumor experienced an average of 65% and 52% reduction in tumor size relative to controls which were immunized with the control vaccine. Furthermore, antibody titers in mice receiving the vaccine compositions containing growth factors were significantly higher than mice that did not receive the vaccines.

EXAMPLE 12

Effect of the Heparin Binding Domain Peptide of bFGF on the Growth of B16BL6 or HUVEC Tumor Cells In Vitro As demonstrated in Example 9, the heparin binding domain peptide of bFGF exhibited an inhibitory effect on bFGF stimulated HUVEC proliferation. The same effect was not seen when incubated with the tumor cells in vitro.

B16BL6 melanoma were plated at 10,000 cells/well in a 24 well plate and incubated overnight. Various concentrations of the heparin binding peptide were added to the wells, followed by addition of media containing 5 ng/ml bFGF. bFGF added in the absence of peptide did not increase proliferation of B16BL6 beyond that of the media control. In addition, no significant effect on the growth of B16BL6 cells was observed when incubated with the heparin binding peptide, as determined by cell counts. The results are provided in FIG. 10. This example provides methods useful for selecting peptides useful for the methods and compositions of the present invention.

EXAMPLE 13

Inhibition of Growth and Development of LLC-LM Metastases in Mice Vaccinated with the Heparin Binding Domain Peptide of bFGF Efficacy of vaccination of mice with the heparin binding domain peptide bFGF in a liposome format was determined in the LLC-LM experimental metastatic model.

Figure 11:
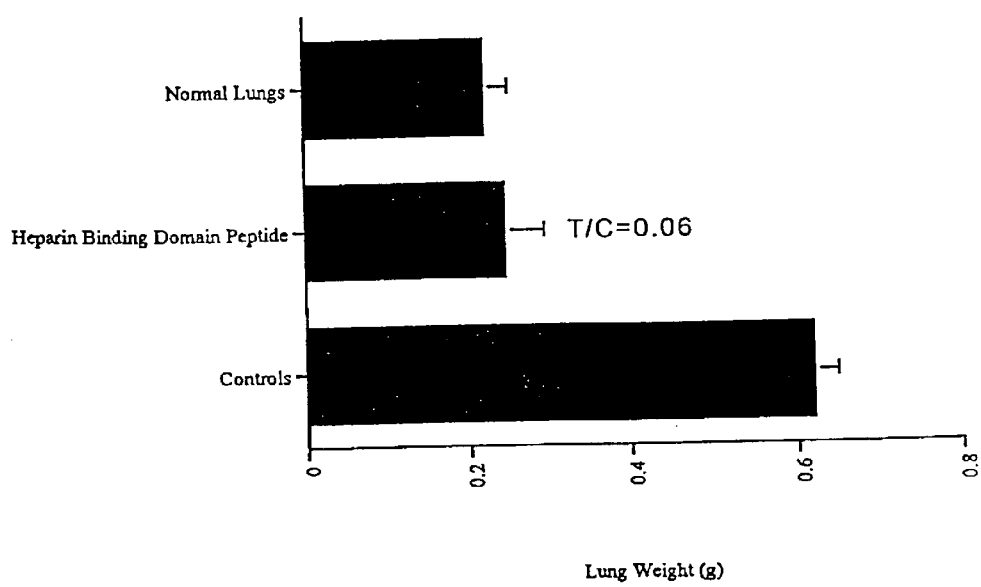
FIG. 11 is a bar graph showing the inhibition of growth and development of LLC-LM metastases in mice vaccinated with the heparin binding domain peptide of bFGF.
Figure 12:
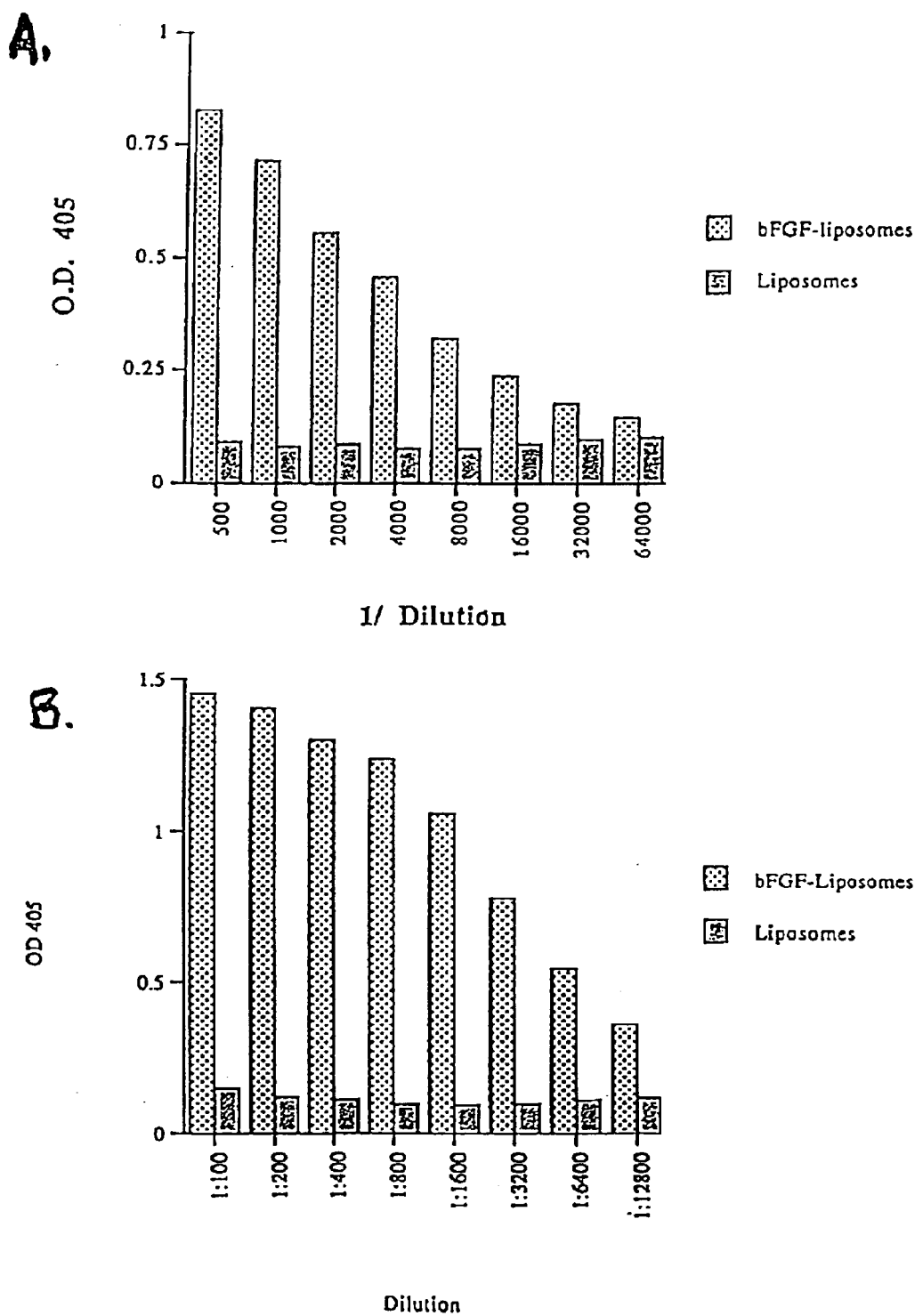
FIGS. 12($a$) and 12($b$) provide graphs showing anti-bFGF titer in serum from mice vaccinated with bFGF-liposomes or control liposomes. The data presented by the graphs represents reactivity of serum from groups of 5 vaccinated mice that was collected on day 35, pooled, serially diluted, and analyzed for reactivity to whole bFGF by measuring absorbance in an ELISA assay.

Mice were vaccinated with the heparin binding domain peptide of bFGF in a liposome format using the same vaccination regimen as in the B16BL6 experiments above (3 inoculations two weeks apart). Two weeks following the final boost, mice were intravenously challenged with LLC-LM. At day 17, the control (no treatment) mice began to succumb to the tumor burden in the lung. All groups were sacrificed. Lungs were removed and analyzed based on lung weight. Normal lung weight was subtracted out of the treated and non-treated groups to determine the T/C. Vaccination with the heparin binding domain peptide inhibited the growth and development of LLC-LM experimental metastasis by 94% when compared to control. These lungs have been photographed and will be assessed histologically. As demonstrated by the results in FIG. 11, the growth and development of metastases was significantly inhibited in mice vaccinated with the heparin binding domain peptide.

EXAMPLE 14

Immunogenicity of Growth Factor Comprising Vaccine Compositions

In Vivo Studies for Demonstrating the Immunogenic Effects of VEGF Peptides in Mice The present example involved the use of vaccine compositions comprising growth factors peptides, specifically vascular endothelial growth factor (VEGF) peptide fragments, incorporated into liposomes such that the compositions were immunogenic for the growth factor peptide when administered to a human or animal. A successful immunogenic response was obtained in mice when VEGF peptides were incorporated into the liposomes via either active peptide conjugation or passive encapsulation.

A. VEGF Peptides

Three different murine VEGF peptides, denominated as Peptides C–E, were incorporated into the liposomes. Peptide C, SEQ ID NO: 3 is a carboxyl terminal peptide that consists of residues 10–115, the six amino acids of exon 8, and an amino-terminal cysteine for cross-linking purposes. Peptide D, SEQ ID NO:4 also a carboxyl terminal peptide, contains residues 102–115, the six amino acids of exon 8, and an amino-terminal cysteine for cross-linking purposes. Peptide E SEQ ID NO:5 is an amino terminal peptide corresponding to residues 1–20 of VEGF with a C-terminal cysteine added for cross-linking purposes. The amino acid sequences of each peptide are provided below: Peptide C CRTKPEKCD-KPRR (SEQ. ID NO:3) Peptide D CECRPKKDRTKPE-KCDKPRR (SEQ. ID NO:4) Peptide E APTTEGEQKSHE-VIKFMDVYC (SEQ. ID NO:5)

B. Vaccine Preparation Using Liposomes i. Active Peptide Conjugation

One method used to incorporate growth factor peptides into liposomes involved chemical coupling of the peptide to amino acids via a thiol group. In these studies, a thiol-reactive liposome was created by using an analog of cholesterol, PDS-CHOL. The PDS-CHOL was first created according to the method of White et al. Vaccine 12(2): 1111–22(1995) Thiocholesterol (Aldrich Chem., #13,611–5 Milwaukee, Wis.) (1.772 g) was dissolved in chloroform, while in a separate vial PDS (2', 2'-dipyridylsulfide or Aldrithiol-2 from Aldrich Milwaukee, Wis.) (1.982 g) was dissolved in a 100:1 mixture of choloroform:glacial acetic acid. The thiocholesterol was added dropwise, at a rate of approximately 30 drops per minute, to the vigorously mixing PDS. The vial was then purged with nitrogen, sealed, covered with foil, and mixed overnight at room temperature. After a stream of nitrogen was used to evaporate the solvent, the sample was recrystallized by adding 50 ml of approximately 56° C. ethanol, placing the sample on ice for one hour, and then placing it at −20° C. for two days. The sample was recovered by filtration with ice cold ethanol and desiccated. Purity was determined to be 90–95% using thin-layer chromatography and an iodine vapor.

Once the PDS-CHOL was prepared, it was combined in a 100 ml round bottom flask with lipids, dimyristoyl phosphatidylcholine (DMPC), dimyristoyl phosphatidylglycerol (DMPG), cholesterol (CHOL), and Lipid A to produce a mole ratio of 9:1:7.4:2:0.02 (DMPC:DMPG:Cholesterol:PDS:Chol:LipidA) (mol:mol). The lipid mixture was rotary evaporated with nitrogen and desiccated. All manipulations were carried out anaerobically using degassed liquids except for final PBS wash. The peptides were then dissolved in 10 mM acetic acid to a concentration of 5 mg/ml and the equivalent of 1 mg was diluted in 6.4 ml de-ionized water. This peptide hydration solution was added to the desiccated liquid, re-suspended via bath sonication, briefly vortexed, and mixed on an orbital shaker overnight at room temperature. The mixture was then lyophilized. Liposomes were pre-formed by adding 2.135 ml citrate/phosphate buffer (0.1 M) and vortexing for 1–2 minutes. Additional peptides were dissolved in sterile 10 mM acetic acid at a concentration of 10 mg/ml, and 0.2 ml (2 mg) was added to the pre-formed vesicles. The mixtures was covered with foil and mixed overnight on an orbital shaker at room temperature. After washing two times with PBS, the liposomes were analyzed for incorporation using BCA (Bicinchroninic acid, Pierce Chemical Co. Rockford, Ill.) (see Bartlett et al. J. Bio. Chem. 234:466–68 (1959) for an explanation of the assay used). The results of the incorporation assay indicated that there was 68%, 74%, and 66% conjugation of peptides C, D, and E, respectively.

ii. Passive Encapsulation

Another method used to incorporate the peptides of growth factors such as VEGF was passive, or simple encapsulation. Again, lipids were aliquotted into depyrogenated 100 ml round bottom flasks in the following order: lipid A in 1:1 chloroform:methanol, DMPC, DMPG, and cholesterol. The lipids were rotary evaporated to remove the bulk solvent and then desiccated. To hydrate the lipids, 4.5 ml sterile de-ionized water was added, the mixture was sonicated and allowed to stand at room temperature for two hours. After transfer to vaccine vials, the mixture was lyophilized. The peptide solutions (2.5 mg/ml in room temperature PBS from a 10 mg/ml stock in acetic acid) were added to the lyophilized lipid and the vials were vortexed vigorously for 2 minutes. The final concentration with respect to the phospholipid was approximately 100 mM. To allow for encapsulation, the vials were placed at 4° C. for 24 hours and then were washed two times with PBS. Subsequent analysis of encapsulation indicated that there was 33%, 19%, and 19% encapsulation of peptides C, D, and E, respectively.

C. Analysis of Vaccine Efficacy

Five Balb/cByJ mice, 6–8 weeks old, were immunized by intraperitoneal injection with liposomes containing one of the three previously described peptides of VEGF incorporated either via active conjugation or passive encapsulation. The target dose was approximately. 10–50 μg of peptide plus 100 μg of Lipid A. Serum was collected on day 35 and analyzed for anti-VEGF activity by ELISA. As a control, mice that were not injected with liposomes were also bled for anti-VEGF peptide titers.

Figure 16:
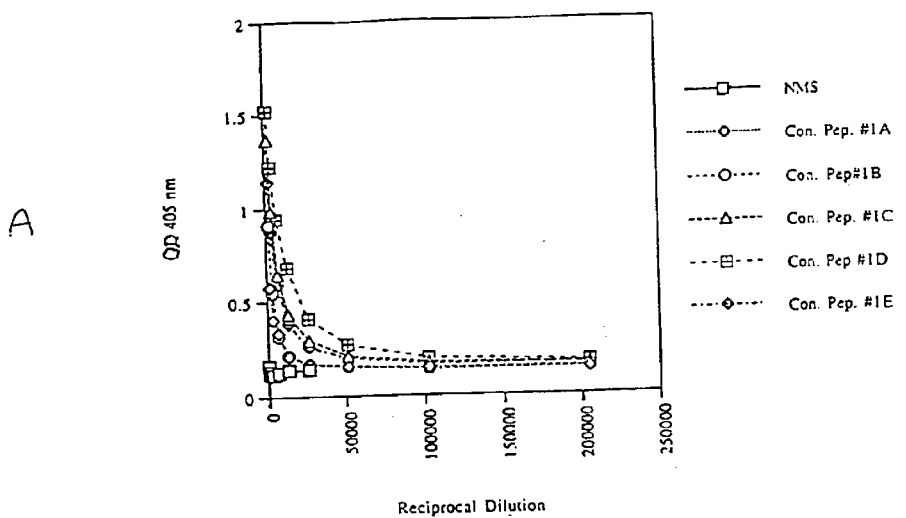
FIGS. 16($a$)–($c$) are graphs demonstrating the immunoreactivity of test peptides to autologous peptide fragments of VEGF. As discussed in Example 13, Balb/cByJ mice were vaccinated with liposomes containing VEGF peptides 1–3 incorporated in the liposome by conjugation according to the protocols outlined in the present invention. Serum from individual mice was collected on day 35, serially diluted, and analyzed for reactivity to autologous peptide fragments of VEGF by measuring absorbance in an ELISA assay. The NMS control demonstrates the reactivity of serum from non-vaccinated mice and is not different from the reactivity of serum from mice vaccinated with a liposome control.
Figure 16:
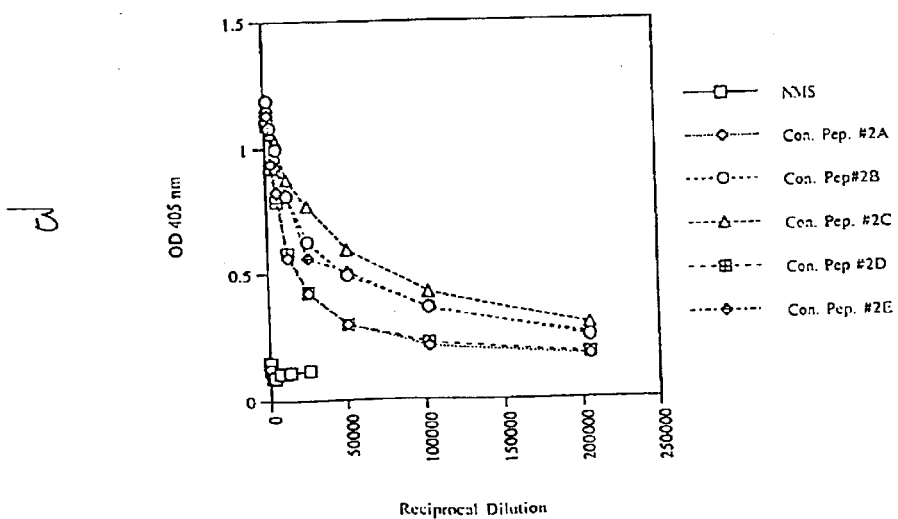
Figure 16:
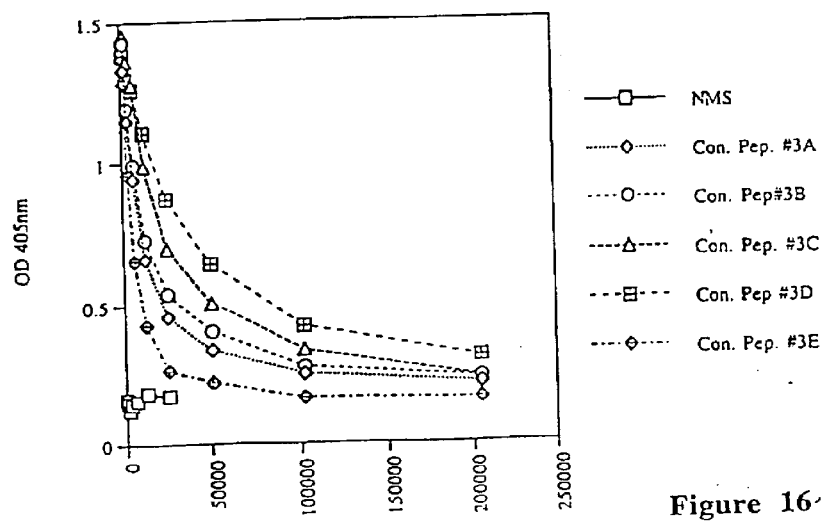

Preliminary data derived from VEGF-peptide-liposome-vaccinated and control Balb/cByJ mice indicate that VEGF vaccine stimulates an anti-VEGF antibody response. When the peptides were conjugated to the liposome, individual Balb/cByJ mice responded with anti-VEGF peptide titers of greater than 1:100,000 for peptides 2 and 3 and titers of 1:25,000 for peptide C (FIGS. 16(a)–(c)). For peptides incorporated by simple encapsulation, individual Balb/cByJ mice responded with anti-VEGF peptide titers ranging from 1:12,500 to 1:50,000 for peptides D and E (FIGS. 17(a)–(c).

The above experiment reasonably demonstrate that a vaccine composition comprising a growth factor, or particularly a peptide epitope of vascular endothelial growth factor, incorporated into a liposome, either by encapsulation or conjugation, can elicit a significant antibody response in vivo.

EXAMPLE 15

Inhibition of the Growth and Development of B16BL6 Experimental Metastasis in Mice Vaccinated with a VEGF Peptide in a Liposome Format A synthetic peptide generated to the neuropilin receptor binding domain of VEGF (Peptide F, SEQ ID NO: 6) was covalently conjugated to liposome vesicles containing lipid A. Mice were vaccinated with Peptide F liposome preparation utilizing the same vaccine regimen as the bFGF peptide vaccines. Two weeks following the final boost, mice were intravenously challenged with B16BL6. Mice were sacrificed at day 14 following challenge. Vaccination with the Peptide F liposome formulation resulted in significant inhibition of B16BL6 experimental metastasis when compared to liposomal lipid A controls (T/C=0.33). The heparin binding domain peptide bFGF covalently linked to liposomes was used as a positive control in this experiment. The results of this experiment are provided in FIGS. 11 and 18.

While this invention has been described in specific detail with reference to the disclosed embodiments, it will be understood that many variations and modifications may be effected within the spirit and scope of the invention.

What is claimed is:

1. An immunogenic composition comprising an immunogenic peptide fragment of vascular endothelial growth factor, wherein the immunogenic peptide fragment consists of SEQ ID No: 3, SEQ ID No: 4, SEQ ID No: 5, SEQ ID No: 6, SEQ ID No: 7, SEQ ID No: 8, or SEQ ID No: 9; and a pharmaceutically acceptable carrier.

2. The composition of claim 1, wherein the pharmaceutically acceptable carrier comprises liposomes, colloidal gold, and carrier proteins.

3. The composition of claim 2, wherein the carrier protein comprises maltose binding protein, bovine serum albunim, keyhole lympet hemocyanin, ovalbumin, flagellin, thyroglobulin, serum albumin, gamma globulin, syngeneic cells, and polymers of D- and/or L-amino acids.

4. The composition of claim 2, further comprising adjuvants, preservatives, diluents, emulsifiers, and stabilizers.

5. The composition of claim 4, wherein the adjuvant is selected from the group consisting of lipophilic muramyl dipeptide derivatives, nonionic block polymers, aluminum hydroxide, aluminum phosphate, lipid A, Freund's incomplete adjuvant, Freund's complete adjuvant, polydispersed β-(1,4) linked acetylated mannan, polyoxyethylene-polyoxypropylene copolymer adjuvants, saponin derivative adjuvants, killed Bordetella pertussis, lipopolysaccharide of gram-negative bacteria, polymeric anions, dextran sulfate, inorganic gels, alum, aluminum hydroxide, and aluminum phosphate.

6. The composition of claim 1, further comprising a hydrophobic moiety attached to the immunogenic peptide.

7. The composition of claim 6, wherein the hydrophobic moiety comprises at least one long chain fatty acid having at least 10 carbon atoms in the lipid backbone.

8. The composition of claim 6, wherein the hydrophobic moiety is selected from the group consisting of palmitic acid, stearic acid, myristic acid, lauric acid, oleic acid, linoleic acid, and linolenic acid.

9. An immunogenic composition comprising an immunogenic peptide fragment of vascular endothelial growth factor, wherein the immunogenic peptide fragment consists of SEQ ID No: 6, and a pharmaceutically acceptable carrier.

* * * * *